(12) United States Patent
Kim et al.

(10) Patent No.: US 12,352,720 B2
(45) Date of Patent: Jul. 8, 2025

(54) REDOX PROBING FOR CHEMICAL INFORMATION

(71) Applicants: University of Maryland, College Park, College Park, MD (US); University of Maryland, Baltimore, Baltimore, MD (US)

(72) Inventors: Eunkyoung Kim, Woodstock, MD (US); Gregory F. Payne, Hunt Valley, MD (US); Mijeong Kang, Rockville, MD (US); Reza Ghodssi, Potomac, MD (US); Thomas E. Winkler, Greenbelt, MD (US); George Banis, Silver Spring, MD (US); Christopher Kitchen, Ellicott City, MD (US); Deanna L. Kelly, York, PA (US); William E. Bentley, Annapolis, MD (US)

(73) Assignees: UNIVERSITY OF MARYLAND, COLLEGE PARK, College Park, MD (US); University of Maryland, Baltimore, Baltimore, MD (US)

(*) Notice: Subject to any disclaimer, the term of this patent is extended or adjusted under 35 U.S.C. 154(b) by 354 days.

(21) Appl. No.: 16/465,243

(22) PCT Filed: Dec. 4, 2017

(86) PCT No.: PCT/US2017/064485
§ 371 (c)(1),
(2) Date: May 30, 2019

(87) PCT Pub. No.: WO2018/102808
PCT Pub. Date: Jun. 7, 2018

(65) Prior Publication Data
US 2019/0346400 A1    Nov. 14, 2019

Related U.S. Application Data

(60) Provisional application No. 62/526,576, filed on Jun. 29, 2017, provisional application No. 62/429,610, filed on Dec. 2, 2016.

(51) Int. Cl.
*G01N 27/327* (2006.01)
*G01N 33/49* (2006.01)

(52) U.S. Cl.
CPC ........ *G01N 27/3277* (2013.01); *G01N 33/49* (2013.01)

(58) Field of Classification Search
CPC ........................ G01N 27/3277; G01N 33/49
See application file for complete search history.

(56) References Cited

U.S. PATENT DOCUMENTS 4,929,313 A * 5/1990 Wrighton ............... B82Y 10/00
                                                      204/412
6,016,686 A   1/2000 Thundat
                 (Continued)

OTHER PUBLICATIONS

Medina-Ramos et al., Buffer Effects in the Kinetics of Concerted Proton-Coupled Electron Transfer: The Electrochemical Oxidation of Glutathione Mediated by [IrCl6]2-at Variable Buffer pKa and Concentration, The Journal of Physical Chemistry C, vol. 117, No. 2, pp. 902-912 (2013) (Year: 2013).*
(Continued)

*Primary Examiner* — James Lin
*Assistant Examiner* — Vivian A Tran
(74) *Attorney, Agent, or Firm* — George Likourezos; Carter, DeLuca & Farrell LLP

(57) ABSTRACT

Methods are provided that allow global access to redox-based molecular information by coupling electrochemical measurements with signal processing approaches. More specifically, the disclosure provides methods that rely on the use of redox probes to assay samples for redox activities that act to exchange electrons with the probe thereby generating detectable optical and electrochemical signature signals that can then be assigned to a sample feature of interest. In particular embodiments, the disclosed assay methods are useful for diagnosis and prognosis of disorders, such as (Continued)

schizophrenia, that are found to be associated with a specific redox-based signature within a subject sample.

16 Claims, 20 Drawing Sheets

(56) References Cited

U.S. PATENT DOCUMENTS

| | | | |
|---|---|---|---|
| 2004/0121305 A1* | 6/2004 | Wiegand | G01N 33/5091 435/4 |
| 2005/0213187 A1 | 9/2005 | Leddy et al. | |
| 2007/0209950 A1* | 9/2007 | Althaus | G01N 33/6896 205/792 |
| 2008/0099347 A1* | 5/2008 | Barlag | G01N 27/3277 204/406 |
| 2014/0200151 A1* | 7/2014 | Bahn | G01N 33/6896 506/9 |
| 2014/0332410 A1* | 11/2014 | Ben-Yoav | B01L 3/502761 204/403.01 |
| 2016/0377639 A1* | 12/2016 | Bahado-Singh | G01N 33/50 514/7.7 |
| 2021/0199616 A1* | 7/2021 | Kim | G01N 27/27 |

OTHER PUBLICATIONS

International Preliminary Report on Patentability issued in PCT/US2017/064485 dated Jun. 13, 2019.

Deanna Kelly et al., "ACNP 55th Annual Meeting: Poster Session I—Poster M204", Neuropsychopharmacology, Dec. 1, 2016 (Dec. 1, 2016), pp. S116-S288, XP055449139, Anonymous: "Neuropsychopharmacology vol. 41 (Suppl 1); Dec. 2016", Dec. 1, 2016 (Dec. 1, 2016), XP055449140, Retrieved from the Internet: URL: https://ncbi.nlm.nih.gov/pmc/issues/280747/ [retrieved on Feb. 7, 2018].

Noureddine Touati et al: "Effect of Storage Time and Temperature on the Quality of Fruit Nectars: Determination of Nutritional Loss Indicators", Journal of Food Quality, vol. 39, No. 3, Feb. 2, 2016 (Feb. 2, 2016), pp. 209-217, XP055449725.

Ivana Novak et al: "Electrochemical Characterization of Epigallocatechin Gallate Using Square-Wave Voltammetry", Electroanalysis, vol. 21, No. 9, Jan. 11, 2009 (Jan. 11, 2009), pp. 1019-1025, XP055449817.

Eunkyoung Kim et al: "Redox Probing for Chemical Information of Oxidative Stress", Analytical Chemistry, vol. 39, No. 3, Dec. 29, 2016 (Dec. 29, 2016), pp. 1583-1592, XP55449283.

* cited by examiner

Correlation between reducing capacity and age or BPRS score for schizophrenia group
| | Age (Both Groups) | Brief Psychiatric Rating Scale (BPRS) According to Symptoms (Schizophrenia) | | | | | |
|---|---|---|---|---|---|---|---|
| | | Activation | Negative | Anxiety/Depression | Positive (Psychosis) | Hostility | Total |
| r | -0.55 | +0.36 | -0.17 | -0.74 | -0.64 | -0.41 | -0.41 |
| p | 0.035 | 0.32 | 0.64 | 0.015 | 0.048 | 0.25 | 0.24 |
FIG. 5A
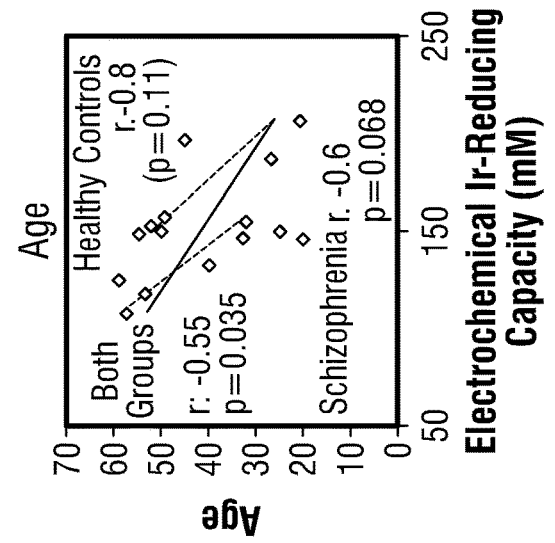
FIG. 5B
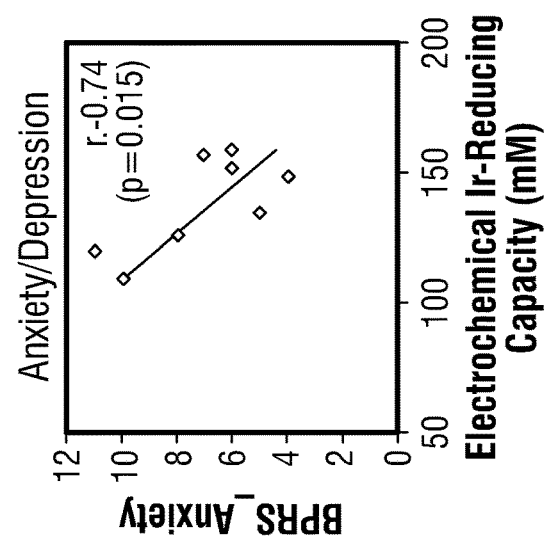
FIG. 5C
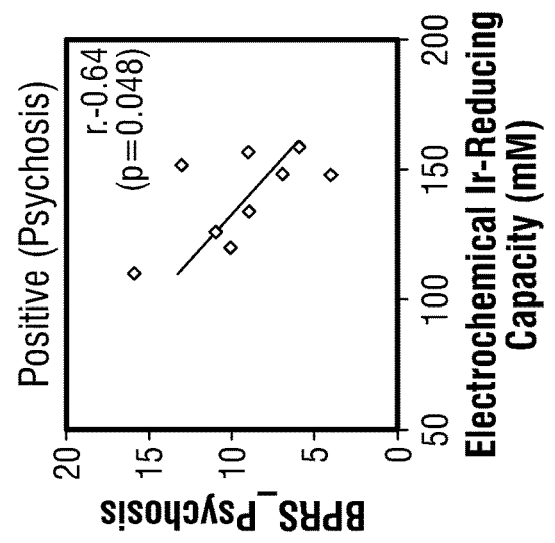
FIG. 5D

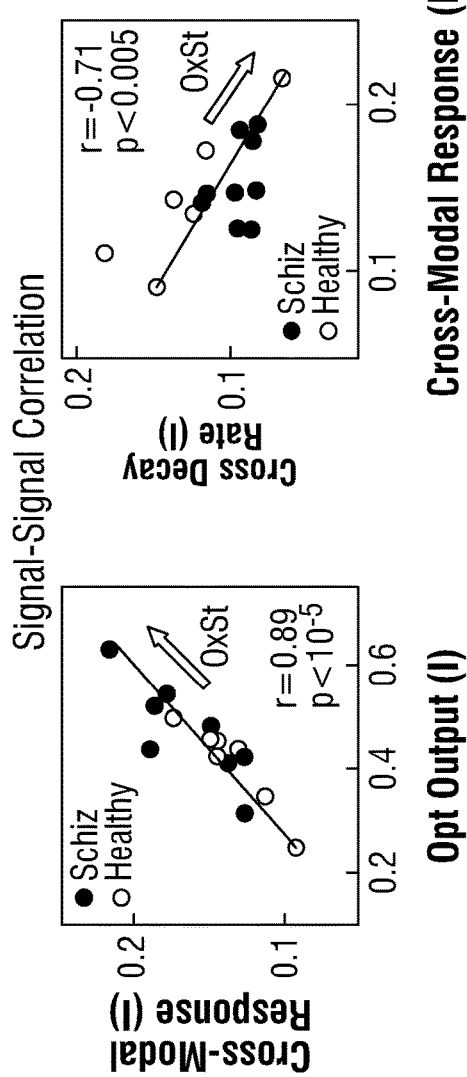
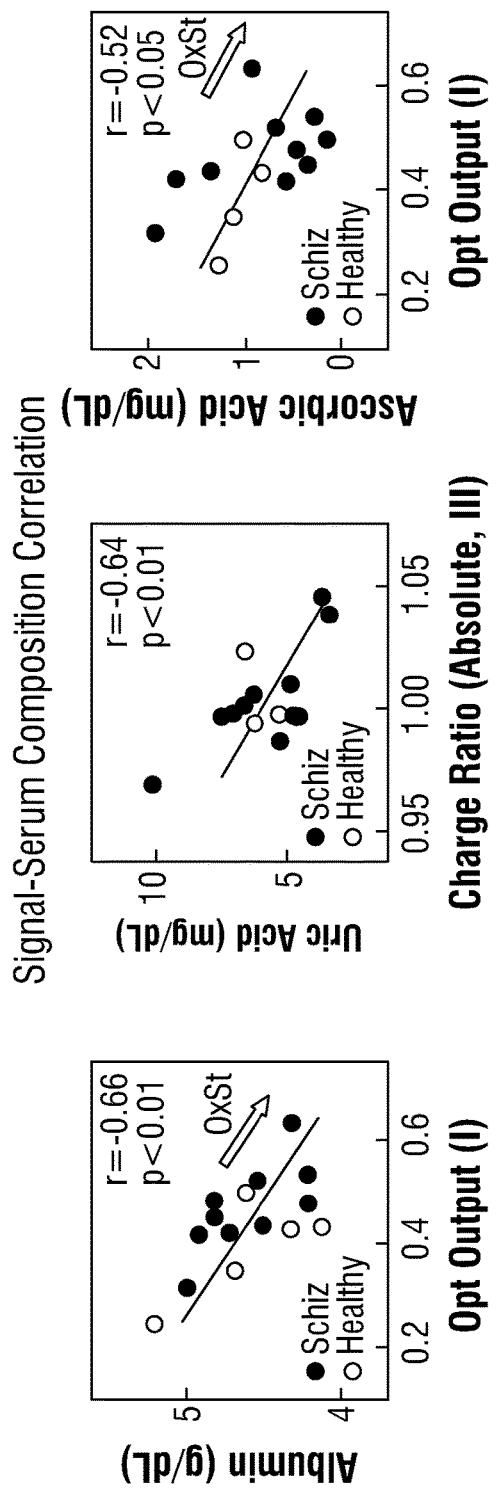
FIG. 8B
FIG. 8C

REDOX PROBING FOR CHEMICAL INFORMATION

CROSS-REFERENCE TO RELATED APPLICATIONS

The present application claims the benefit of U.S. Provisional Patent Application No. 62/429,610 filed on Dec. 2, 2016, entitled "REDOX PROBING FOR CHEMICAL INFORMATION OF OXIDATIVE STRESS" and No. 62/526,576 filed on Jun. 29, 2017, entitled "SPECTRO-ELECTROCHEMICAL DETECTION OF OXIDATIVE STRESS" the entire contents of which are incorporated by reference herein.

GOVERNMENT SUPPORT

This invention was made with government support under grant number CBET1435957 awarded by the National Science Foundation, grant number HDTRA1-13-1-0037 awarded by the DOD/DTRA and grant number MH105571 awarded by the National Institutes of Health. The government has certain rights in the invention.

TECHNICAL FIELD

Methods are provided that allow global access to redox-based molecular information by coupling electrochemical measurements with signal processing approaches. More specifically, the disclosure provides methods that rely on the use of redox probes to assay samples for redox activities that act to exchange electrons with the probe thereby generating detectable optical and electrochemical signature signals that can then be assigned to a sample feature of interest. In particular embodiments, the disclosed assay methods are useful for diagnosis and prognosis of disorders, such as schizophrenia, that are found to be associated with a specific redox-based signature within a subject sample.

BACKGROUND

The analysis of chemically-based redox information within a sample, for example, a biological, soil, air and water sample, can be useful in detecting sample markers, e.g., features, traits, or qualities, of interest within the sample. Traditional approaches to access chemical information in a sample focus on chemically specific analytical methods (e.g., HPLC and mass spectrometry) (8, 9). However, such approaches have wide limitations caused by cost, labor, time and such approaches are not translatable into a variety of fields. With regard to biological samples, increasing evidence links aberrant redox-chemistry to the development of various disorders and diseases that include cancer, inflammation, cardiovascular disease, neurodegenerative diseases, and neuropsychiatric diseases (1-4) to name a few. Accordingly, development of a simple, rapid, objective measurement of redox activities within a sample, which will be useful for both researchers and clinicians, remains a significant challenge in the field.

SUMMARY

Methods are provided that allow access to chemical redox-based molecular information by coupling electrochemical measurements with signaling process approaches. More specifically, the disclosure provides methods that rely on the use of redox probes to assay samples for redox activities that result in the generation of a detectable optical, electrochemical, and/or mechanical signature signal that can be assigned to a specific sample feature, trait, or quality of interest. As used herein, redox probe, redox mediator and electron shuttle are used interchangeably. In such a method, diffusible redox-probes (e.g., mediators or electron shuttles) interactively probe a sample for redox information. In addition, in the presence of electrical inputs, complex redox contexts can be established and dynamic changes can be detected over time which can be used to develop a more distinctive redox-based signature. The methods disclosed herein can be used in two settings. First, the methods can be used to discover a signature signal that can be found to be associated with a sample feature, trait, condition or quality of interest within a sample. Second, the methods described herein, may be used to test a sample for the established signature signal found to be associated with a sample feature, trait, condition or quality of interest within a sample.

The methods of the invention can be used to assay a wide range of different sample types, including for example, soil, water, air, chemical compositions, pharmaceutical compositions, agricultural, environmental and industrial compositions for development of specific redox-based signatures that can be correlated to a specific sample marker of interest. As used herein, "marker" refers to a specific feature, trait, quality or condition of interest associated with the sample. The marker of interest may include, for example, the presence of a disease or disorder state in a subject, the likelihood of responding to a particular disease treatment, or the presence of contaminants in a pharmaceutical composition, industrial composition, food, water or air samples. In one particular aspect, the sample is a biological sample which can be assay to determine the presence of a redox-based signature for diagnosis and/or prognosis of a specific disease or disorder, such as schizophrenia, in a subject.

The present disclosure provides a system for determining the electrochemical signature of a sample comprising the steps of: (i) contacting a sample with at least one redox-mediator; and (ii) detecting the generation of at least one signal that includes but is not limited to a signal indicting the redox-based signature, wherein a change in the redox-based signature compared to a control indicates the presence of a marker of interest. The system may further include the step of (iii) of providing electrical input to the sample as a sequence of oxidative or reductive pulses or oscillating electrical inputs that serve to convert the inert form of the redox-mediator into its oxidized or reduced forms. The output signals can be in the form of a computer executable code.

In embodiments, the disclosed methods provide for (i) the discovery of signature patterns (e.g., markers) or (ii) the routine measurement for comparison against a previously-discovered standard signature pattern (e.g., for diagnosis or assessment). In a specific aspect, a method for assaying for a condition within a subject is provided that relies on the use of a redox-mediator to probe a sample for redox-based chemical information and generate a detectable optical and electrochemical signal which would be used to discover signature patterns or to detect patterns for comparison to previously-established signatures for the purpose of characterizing said condition. Said conditions include diseases or disorders selected from the group consisting of inflammatory, endocrine, cardiovascular, infectious, metabolic based, immunological, infectious, autoimmune, and neurological diseases and disorders to name a few. In certain non-limiting aspects, the condition is a disease or disorder based on redox-dysfunction. As one example, a method for detecting a condition within a sample is provided comprising the steps of: (i) contacting a subject sample with one or more redox-mediators; and (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected it can be assessed whether said signal is associated with a given condition.

In a specific example, a method is provided for detecting a redox-based condition, wherein said condition is associated with the presence of oxidative stress, comprising the steps of: (i) contacting a subject sample with one or more redox-mediators; (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected it can be assessed whether said signal indicates the presence of a condition associated with oxidative stress. For example, in a control sample, the transfer of electrons by a normal level of reducing species within the sample to the redox-mediator produces a specific optical or chemical signal (i.e., the control redox-signature). Accordingly, in a sample derived from a subject having a condition associated with oxidative stress, there is a discernable change in one or more signal metrics (e.g. an attenuation or amplification of an optical absorbance or electrical current), when compared to a control or standard, that is a characteristic indicator of oxidative stress.

In another aspect, a method is provided for detecting a redox-based condition, wherein said condition is schizophrenia, comprising the steps of: (i) contacting a subject sample with one or more redox-mediators; (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected it can be assessed whether said signal possesses the characteristic signatures associated with schizophrenia within the subject. For example, in a control sample, the transfer of electrons by a normal level of reducing species within the sample to the redox mediator produces a specific optical or chemical signal (i.e., the control redox-signature). Accordingly, in a sample derived from a subject having schizophrenia, there is a discernable change in one or more signal metrics (e.g. an attenuation or amplification of an optical absorbance or electrical current), when compared to a control or standard, that is a characteristic indicator of schizophrenia.

In a specific aspect, a method is provided for diagnosis of schizophrenia that utilizes the iridium salt $K_2IrCl_6$ ($Ir^{OX}$) as a redox mediator to detect a sample's reducing activities and this activity can be detected by independent optical and electrochemical modalities. In such an instance, the attenuation of the optical and electrical chemical redox-signal observed in a control sample is increased as compared to a sample derived from a patient having schizophrenia, i.e., there is less signal attenuation in the schizophrenia sample.

A number of different redox-mediators may be used in the disclosed methods. Such mediators include, but are not limited to, those redox-mediators selected from the group consisting of iridium, ferrocene, ferricyanide, ruthenium, osmium, rhodium, copper, cobalt, nickel, chromium, platinum and palladium, or redox-active organic molecules such as phenolics (e.g., acetosyringone), and heterophenols (including aminophenols and chlorophenolindophenols), phenazines (e.g., pyocyanin), organosulfur compounds (tetrathialfulvaene and methylene blue), and radical precursors (viologens or 2,2'-azino-bis(3-ethylbenzthiazoline-6-sulphonic acid).

In a specific aspect, the methods disclosed herein utilize the iridium salt $K_2IrCl_6$ ($Ir^{OX}$) as a redox mediator to detect a sample's reducing activities and this activity can be detected by independent optical and electrochemical modalities. Accordingly, in one aspect of the invention, $K_2IrCl_6$ (designated $Ir^{OX}$) is utilized as a redox-mediator to determine the presence of oxidative stress, or presence of schizophrenia, within a subject sample. $Ir^{OX}$ is a reasonably strong oxidant (34, 35) and has been shown to accept electrons from a broad range of biologically relevant reductants (36) including, for example, GSH,(37) ascorbate,(38) and cysteine.(39) The use of an iridium-based reducing assay has the advantage of a high sensitivity to GSH which is an especially important attribute for probing serum for information on the presence of oxidative stress disorders such as schizophrenia. The transfer of electrons from a reducing species in the sample to the $Ir^{OX}$ mediator results in the generation of both optical and electrochemical signals which are particularly convenient for rapid, point-of-care analysis of samples.

Subject samples that may be used to measure levels of reducing activity in a sample include, for example, blood, sweat, urine, saliva and serum sample. In a specific aspect of the invention, serum samples are utilized in the practice of the disclosed assay methods.

In particular aspects, the methods disclosed herein are useful in the diagnosis, prognosis and monitoring of treated subjects with conditions associated with specific redox-based signatures. The invention is useful in determining or adjusting the treatment of conditions associated with a specific redox-based signature, for example, those manifested by abnormal levels of reducing activity. In a particular embodiment of the invention, the methods disclosed herein can be used in the diagnosis, prognosis or for following the treatment of patients afflicted with schizophrenia which has been shown to be associated with abnormal levels of reducing activity.

In another aspect, a method is provided for monitoring a redox-based condition, wherein said condition is schizophrenia, comprising the steps of: (i) contacting a subject sample derived from a patient being treated for schizophrenia with one or more redox-mediators; (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected, the detected signal is compared to the detected signal in samples derived from the subject as they progress through treatment, wherein it can be assessed whether said signal indicates a response to drug treatment within the schizophrenic subject.

In addition, kits are provided that may be used to detect a redox-based signature within a test subject. Such kits, may comprise, for example, components as described herein for assaying for reducing activity within a sample and instructions for determining the level of reducing activity in the sample isolated from a subject. The kit may further include a means for contacting the sample with an electrical input as a sequence of oxidative or reductive pulses that serve to convert the form of the redox-mediator into its oxidized or reduced form. In one aspect, the test subject can be one suspected of being afflicted with schizophrenia.

BRIEF DESCRIPTION OF THE DRAWINGS

Various embodiments of the present invention are described herein with reference to the drawings wherein:

FIG. 1A shows scheme for redox-probing to access chemical information of oxidative stress. FIG. 1B shows that the $Ir^{OX}$ mediator reports reducing activities of a sample as attenuations in optical and electrochemical signals. FIG. 1C shows optical signal (absorbance) attenuation and FIG. 1D electrochemical signal (reductive charge) attenuation of $Ir^{OX}$ in the presence of a reduced glutathione (GSH). FIG. 1E shows observed signal attenuations of $Ir^{OX}$ when incubated with various reductants (measurements were performed in quadruplicate and error bars indicate standard deviation).

FIG. 2A shows optical signal attenuation and FIG. 2B shows electrochemical signal attenuation relative to the concentration of individual reductants. FIG. 2C shows consumed $Ir^{OX}$ to oxidize individual reductant versus concentration of reductants. FIG. 2D shows the correlation between optical signal attenuation and electrochemical signal attenuation (N=17, r=+0.99). Measurements were performed in quadruplicate and error bars indicate standard deviation.

FIG. 3A is a scheme illustrating commercial Cu-reducing assay. FIG. 3B shows optical signal (absorbance) of CuOX when incubated with various reductants. FIG. 3C shows optical signal increase of CuOX relative to the concentration of individual reductants. FIG. 3D shows GSH sensitivity of Ir-reduction assay compared with other methods (data from Ir-reduction and Cu-reduction assays were experimentally measured while the best fit lines were from Cao et al. (1998) (49). Measurements in parts b-d were performed in triplicate (all error bars indicate standard deviation).

FIG. 4A shows reducing capacity of filtered serum and FIG. 4B shows serum for healthy control (N=5) and schizophrenia (N=10) groups. Reducing capacity was measured by the commercial Cu-reduction method and the Ir-reduction method with both electrochemical and optical detection. FIG. 4C shows measurement of total sulfhydryl groups (—SH) in serum samples of healthy control and schizophrenia groups. FIG. 4D shows a correlation between total sulfhydryl groups and Ir-reducing capacity (electrochemical detection) of serum sample (N=15, r=+0.57, p=0.026). FIG. 4E shows receiver operating characteristic (ROC) curves for electrochemical Ir-reduction method, Cu-reduction method, and Ellman's total sulfhydryls assay for diagnosis of the schizophrenia group from the healthy control group. FIG. 4F demonstrates a correlation between Ir-reducing capacities measured electrochemically and optically (N=15, r=+0.96). Measurements in parts A-C were performed in quadruplicate (error bars indicate standard deviation).

FIG. 5A-D shows a correlation of Ir-reducing capacity with age and symptom severity. FIG. 5A demonstrates correlations between Ir-reducing capacity assay (electrochemical detection) and age or symptoms as measured by the brief psychiatric rating scale (BPRS). FIG. 5B shows a correlation between Ir-reducing capacity and age for healthy control and schizophrenia groups. FIG. 5C shows a correlation between Ir-reducing capacity and anxiety/depression symptom. FIG. 5D shows a correlation between Ir-reducing capacity and positive (psychosis) symptom.

FIG. 8B shows high correlations between signal metrics generated during the first pulse.

FIG. 8C shows correlations between serum components and two signal metrics.

DETAILED DESCRIPTION

Figure 1A:
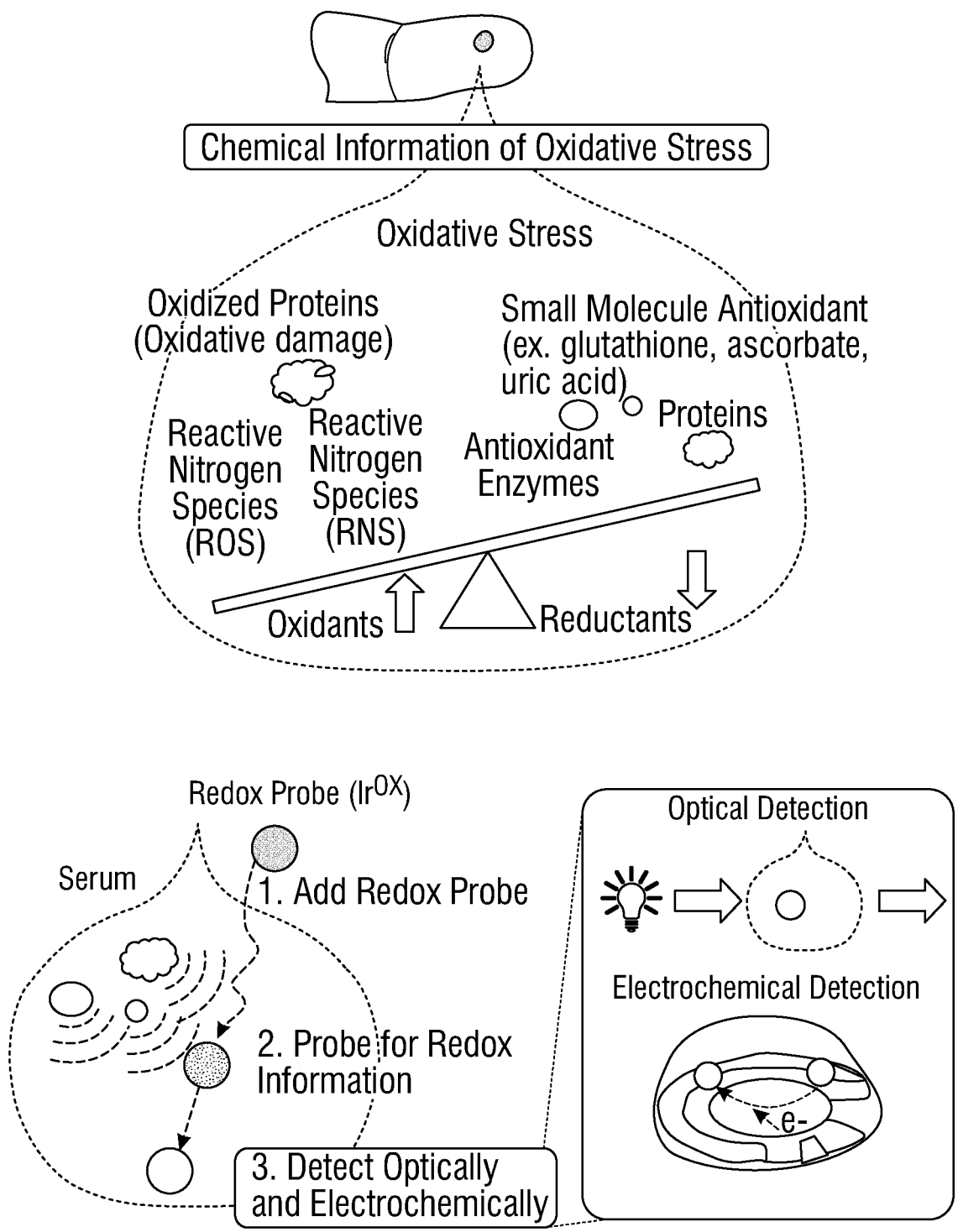
FIG. 1A-E shows qualitative validation of an Ir-reducing assay.

The accompanying drawings, which are incorporated in and constitute a part of the specification, illustrate embodiments of the disclosure and, together with a general description of the disclosure given above, and the detailed description of the embodiment(s) given below, serve to explain the principles of the disclosure.

Methods are provided that allow access to chemical redox-based molecular information by coupling convenient measurements such as multimodal spectroelectrochemical measurements with signal processing approaches. More specifically, the disclosure provides methods that rely on the use of redox probes to assay samples for reducing activities that result in the generation of a detectable optical and electrochemical signature signal that can be assigned to a specific sample feature, trait, or quality of interest ("marker") within the sample. In such a method, diffusible redox-active species (e.g., mediators or electron shuttles) interactively probe a sample for redox information and, when present, imposed electrical inputs establish complex redox contexts that can be used to develop a redox-based signature.

The methods of the invention can be used to assay a wide range of different sample types, including for example, soil, water, air, chemical compositions, pharmaceutical compositions, agricultural and industrial compositions for development of specific redox-based signatures that can be correlated to a specific sample marker of interest. For example, a soil sample can be probed using the methods provided herein to determine the chemical and biological features of the soil. In yet another example, an air sample may be analyzed to detect certain characteristics (e.g., pollutants) in the air.

In certain aspects of the invention, a spectroelectrochemical reaction cell containing specific redox mediators and a means for providing electrical input, may be placed in a specific environmental medium, where the environmental medium diffuses into the cell, to determine the electrochemical signature of that environment. For example, an electrochemical or spectroelectrochemical device may be placed in a specific environment (for example, air, water, soil, reaction or manufacturing vessel) of interest, for detection of the redox signature, e.g. marker, of interest.

As disclosed herein a signal pattern, signature pattern, electrochemical signature, or spectroelectrochemical signature are used interchangeably, can be found to be associated with a specific feature, trait, quality or condition of interest found within a sample. The specific feature, trait, quality or condition of interest may include, for example, the presence of a disease or disorder state in a subject, the likelihood of responding to a particular disease treatment, or the presence of contaminants in a pharmaceutical composition, industrial composition, food, water or air samples. In one particular aspect, the sample is a biological sample which can be assay to determine the presence of a signature pattern for diagnosis and/or prognosis of a specific disease or disorder, such as schizophrenia, in a subject.

In a specific embodiment, a method for assaying for a condition within a subject is provided that relies on the use of a redox-mediator to probe a sample for redox features. These features are detectable by optical and electrochemical measurements associated with reactions of the mediator, e.g., by a respective sensor. In aspects, the sensor may include an optical sensor. These measurements are the signals that form a signature signal known to be characteristic for said condition. In certain aspects, the condition is a disease or disorder based on redox-dysfunction. As one example, a method for detecting a condition within a sample is provided comprising the steps of: (i) contacting a subject sample with one or more redox-mediators; and (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected it can be assessed whether said signal is associated with a given condition.

In a specific aspect of the invention, subject biological samples can be analyzed to develop a specific redox-based electrochemical signature that can act as a marker for the presence of a certain condition wherein said condition is a disorder or disease. As one example, the disclosed methods may be used to assay for the presence of a redox-based condition wherein the condition is one of redox-dysfunction within a subject. Such redox-dysfunction can result from damage caused by reactive oxygen species (and other reactive species) and is regarded as an imbalance between pro-oxidant and anti-oxidant activities. Such disorders, including, for example, cancer, inflammation, cardiovascular disease and mental health disorders. inflammation and are integral features of abnormal redox-reactions.

The present disclosure provides simple, rapid, and robust methods to probe subject samples for chemical information relevant to redox-reactions in a subject sample, for example, for detection of redox-dysfunction. The present disclosure is based, at least in part, on the observation that the level of reducing activity in a serum sample can be measured through the use of redox-mediators that generate detectable optical and electrochemical signals upon electron transfer. Such redox-mediators may also be used in conjunction with an electrical input as a sequence of oxidative or reductive pulses that serve to convert the form of the redox-mediator into its oxidized or reduced form for detection of pattern signatures from dynamic changes over time. As exemplified in the working examples, such methods can be used for assaying for the presence of schizophrenia within a subject.

In a specific example, a method is provided for detecting a redox-based condition, wherein said condition is associated with the presence of oxidative stress, comprising the steps of: (i) contacting a subject sample with one or more redox-mediators; (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected it can be assessed whether said signal indicates the presence of a condition associated with oxidative stress. For example, in a control sample, the transfer of electrons by a normal level of reducing species within the sample to the redox-mediator produces a specific optical or chemical signal (i.e., the control redox-signature). Accordingly, in a sample derived from a subject having a condition associated with oxidative stress, there is a discernable change in one or more signal metrics (e.g. an attenuation or amplification of an optical absorbance or electrical current), when compared to a control or standard, that is a characteristic indicator of oxidative stress.

In another aspect, a method is provided for detecting a redox-based condition, wherein said condition is schizophrenia, comprising the steps of: (i) contacting a subject sample with one or more redox-mediators; (ii) detecting the produced optical and/or chemical signals. The method may further include contacting the sample with an electrical input as a sequence of oxidative or reductive pulses that serve to convert the form of the redox-mediator into its oxidized or reduced form. Once the produced optical and/or chemical signals have been detected it can be assessed whether said signal indicates the presence of schizophrenia within the subject. For example, in a control sample, the transfer of electrons by a normal level of reducing species within the sample to the redox mediator produces a specific optical or chemical signal (i.e., the control redox-signature). Accordingly, in a sample derived from a subject having schizophrenia, there is a discernable change in one or more signal metrics (e.g. an attenuation or amplification of an optical absorbance or electrical current), when compared to a control or standard, that is a characteristic indicator of schizophrenia.

The provided assay methods for detecting a redox-based condition are based on the ability to measure the transfer of electrons by a wide range of sample components (reductants), within a patient sample, to a redox-mediator and in doing so generate a detectable optical and chemical signal. Such reductants can be detected through the use of redox-mediators that accept the transferred electrons. Such redox-mediators include, for example, those redox-mediators selected from the group consisting of iridium, ferrocene, ferricyanide, ruthenium, osmium, rhodium, copper, cobalt, nickel, chromium, platinum and palladium, or redox-active organic molecules such as phenolics (e.g., acetosyringone), and heterophenols (including aminophenols and chlorophenolindophenols), phenazines (e.g., pyocyanin), organosulfur compounds (tetrathialfulvaene and methylene blue), and radical precursors (viologens or 2,2'-azino-bis(3-ethylbenzthiazoline-6-sulphonic acid).

The choice of the redox-mediator to be used in the disclosed methods will rely on the type of sample being tested and the desired marker being searched for. A given redox-mediator can be chosen for a specific reaction because of its unique reactivities. In some instances, redox-mediators with varying redox potentials may be used. In some instances, multiple redox-mediators may be used and tested to determine the quality and quantity of redox-mediators that are then subsequently used to provide the greatest ability to discriminate between a control sample and a sample having the particular marker of interest. Additionally, the sample may be contacted with the redox-mediator for different periods of assay times. In one, non-limiting example, the sample may be contacted with the redox-mediator for 30 minutes. In other examples, the sample may be contacted with the redox-mediator for periods of time greater than or less than 30 minutes. The contact times to be used are those that provide the greatest ability to discriminate between a control sample and a sample having the particular marker of interest or balance the needs for other factors (e.g., assay speed and convenience), and can be determined by one or ordinary skill in the art. In addition to redox-mediators, the sample may further be provided with an electrical input as a sequence of oxidative or reductive pulses or oscillating electrical inputs that serve to convert the form of the redox-mediator into its oxidized or reduced form. Such dual modality reactions, which utilize multiple redox-mediators as well as varied electrical inputs, permit the detection of unique and distinctive signatures from dynamic changes over time.

In a specific aspect, the methods disclosed herein utilize the iridium salt $K_2IrCl_6$ ($Ir^{OX}$) as a redox mediator to detect a sample's reducing activities and this activity can be detected by independent optical and electrochemical modalities. Accordingly, in one aspect of the invention, $K_2IrCl_6$ (designated $Ir^{OX}$) is utilized as a redox-mediator to determine the presence of oxidative stress, or presence of schizophrenia, within a subject sample. $Ir^{OX}$ is a reasonably strong oxidant (34, 35) and has been shown to accept electrons from a broad range of biologically relevant reductants (36) including, for example, GSH, (37) ascorbate,(38) and cysteine (39). The use of an iridium-based reducing assay has the advantage of a high sensitivity to GSH which is an especially important attribute for probing serum for information on the presence of oxidative stress or schizophrenia. The transfer of electrons from a reducing species in the sample to the $Ir^{OX}$ mediator results in the generation of both optical and electrochemical signals which are particularly convenient for rapid, point-of-care analysis of samples.

In certain aspects, methods include contacting the sample with redox-mediators in conjunction with an electrical input as a sequence of oxidative or reductive pulses or oscillating electrical inputs that serve to convert the form of the redox-mediator into its oxidized or reduced form. The electrical input is in the form of that the oxidative voltages can at one time be above and at another time be below the mediator's standard redox potential $E^0$ values. Cyclic voltammetry (CV) experiment can be performed, for example, over several hours. The use of redox-mediators, in combination with electrical input can detect patterns from dynamic changes overtime resulting in more sensitive assays Subject samples that may be used to assay for a specific redox-based condition, include, for example, biological samples such as blood, sweat, urine, saliva and serum samples. In a specific aspect of the invention, serum samples are utilized in the practice of the disclosed assay methods. According to some embodiments the serum is purified, or isolated away from other blood components, in a collected blood specimen. In another embodiment, serum samples are further filtered to remove bio-macromolecules (MW>10 dDa) prior to testing of the serum sample. Further, the serum sample may be diluted prior to use in the disclosed assay methods. Serum may be diluted depending on signal strength and dilutions may range from 5× to 10,000×. Methods for purification of serum from collected blood samples are routine and well known to those of skill in the art.

Measurements of the optical and/or electrochemical output signals, and comparisons to normal control levels, allow one to assess for the presence of a redox-mediated condition within the subject. In such an instance, an alteration in the optical and electrochemical signal (redox-signature), as compared to control levels, can indicate the presence of the specific feature, trait, quality or condition of interest. "Alteration" as it relates to measured optical and electrochemical signaling, refers to statistically significant alterations (increases or decreases) of individual or combinations of signal metrics as would be recognized by persons skilled in the relevant art.

Determining, measuring or quantifying the level of electrochemical activity within a test sample may be performed by a variety of methods well known in the art. For example, the methods and assays of the invention may include, without limitation, the use of a redox-mediator coupled with detection of optical and electrochemical signals. For optical signal, recordings can be made using a microplate reader. For iridium based assays, the absorbance is measured at 488 nm. For electrochemical measurements, cyclic voltammetry (CV), chronocoulometry (CC), or specific sequence of electrical pulses may be performed, for example, to measure the electrochemical signal.

In a specific aspect of the invention, $Ir^{OX}$ is added to a diluted serum sample and the mixture is allowed to undergo redox reactions with electron transfer from serum components to $Ir^{OX}$ to $Ir^{RED}$. An optical modality is based on the observation that the oxidized $Ir^{OX}$ has a strong absorbance at 488 nm while $Ir^{RED}$ has little absorbance. An electrical modality is based on an electrochemical titration of the remaining oxidized $Ir^{OX}$. If $Ir^{OX}$ is reduced during incubation with the serum sample, then attenuations will be observed in both end-point optical and electrical measurements. Accordingly, lower observed reducing activities are associated with redox-dysfunction. Thus, in samples derived from subjects suffering from redox-dysfunction, there will be an observed alteration in both optical and electrical measurements as compared to samples derived from control or normal subjects.

In an aspect of the invention, which can increase the discriminating power of the assay methods, an assay system is provided to access redox-based molecular information within a sample globally by coupling electrochemical measurements with signal processing approaches. In such an assay system, the chemical input comprises one or more diffusible redox-active species (e.g., mediators or electron shuttles) that can exchange electrons with a wide range of components and report electron exchange by redox-state-dependent optical and electrical outputs. The electrical input comprises a sequence of oxidative voltage pulses or oscillating electrical inputs that serve to convert the inert reduced forms of the mediators into an oxidized form which diffuses into the sample in "search" of electron-rich components. The output optical and electrical responses can be measured simultaneously using a perforated electrode in a spectroelectrochemical cell and can be used to detect the presence of redox-based signatures within a sample.

Through the use of multiple redox-mediators in combination with oxidative voltage pulses or oscillating electrical inputs, electrochemical signatures may be identified that correlate with a specific condition or, which correlate with the severity of said disorder, or with an indication of successful treatment of a disease or disorder. In a specific aspect, a serum sample can be probed with a single mediator and imposed voltages can be imposed that at one time is above and at another time is below the mediator's $E^0$ value. In another aspect of the assay system, redox probing may be extended from use of one redox-mediator to use of multiple redox-mediators and probed over a broader range of voltages to detect more diverse redox interactions. A spectroelectrochemical cell can be used to impose diverse electrical inputs and detect optical and electrochemical responses over several hours.

The disclosed methods for detecting redox-based conditions may be used for diagnosis or prognosis of a test subject who is afflicted with a chronic, or acute disorder, or a flare-up (i.e., a sudden appearance or worsening of the symptoms of a disease or condition) associated with a redox-dysfunction state. According to embodiments of the invention, detection of a level of reducing activity in a subject sample that is significantly lower than its level in a healthy control subject sample indicates an unfavorable redox-condition in said subject. Such disorders include, but are not limited to, inflammation, cancer, cardiovascular disease, neurodegenerative disease and neuropsychiatric diseases to name a few. In a particular embodiment, the disorder is schizophrenia.

In another aspect, a method is provided for monitoring a redox-based condition, wherein said condition is schizophrenia, comprising the steps of: (i) contacting a subject sample derived from a patient being treated for schizophrenia with one or more redox-mediators; (ii) detecting the produced optical and/or chemical signals. The method may further include contacting the sample with an electrical input as a sequence of oxidative or reductive pulses or oscillating electrical inputs that serve to convert the form of the redox-mediator into its oxidized or reduced form. Interactions of the mediators with sample components can be detected to generate optical and/or chemical signals, the detected signal is compared to the detected signal in samples derived from an untreated subject, wherein it can be assessed whether said signal indicates a response to drug treatment within the schizophrenic subject.

As disclosed herein, a system is provided to execute the described method of the present invention. In embodiments, the disclosed systems provide for (i) the discovery of signature patterns (e.g., markers) or (ii) the routine measurement for comparison against a previously-discovered standard signature patter (e.g., for diagnosis or assessment). In various embodiments, determining electrochemical or spectroelectrocemical signature of samples may include a software program that is capable of accessing the resultant electrochemical or spectroelectrocemical signature and correlating the signature to a trait or property. The step of correlating may include comparing the resultant signature to a control or a database of signatures.

In one embodiment, a system for implementing the above-described method may include (i) an identification module programmed to identify executable code of the electrochemical or spectroelectrocemical signature that is to be analyzed; (ii) an analyzer module programmed to perform analysis of the executable code to identify one or more objects which the executable code may be used to compare and correlate the data of the signature; (iii) an identification module programmed to use a result of the analysis to track the one or more objects identified during the analysis; (iv) an output module programmed to provide the output in terms of the sample or property of interest, and (v) at least one computer processor configured to execute the identification module, the analyzer module, the identification module and output module. In some embodiments, the analyzer module may further include a training module to train the analyzer to identify and correlate the signature that discriminates the sample and control data set and/or may include a feedback module that autonomously adjusts the input stimuli to discover inputs that generate signatures with greater discriminating capabilities. Any executable training method or feedback method performed by a computer is considered to be within the scope of the invention.

In examples, the above-described method and system may be encoded as computer-readable instructions on a computer-readable-storage medium. One or more computer systems may be utilized with one or more executable instructions having one or more storage mediums. For example, a computer-readable-storage medium may include one or more computer-executable instructions that, when executed by at least one processor of a computing device, may cause the computing device to (i) identify executable code of the electrochemical signature; (ii) to analyze the executable code and compare and correlate the data of the signature; (iii) to track the one or more objects identified during the analysis, (iv) to provide feedback that autonomously adjusts the input stimuli to discover inputs that generate signatures with greater discriminating capabilities and (iv) output the result of the sample or property of interest.

In addition, kits are provided that may be used to detect a redox-based signature within a test subject. Such kits, may comprise, for example, components as described herein for assaying for reducing activity within a sample and instructions for determining the level of reducing activity in the sample isolated from a subject. The kit may further include a means for contacting the sample with an electrical input as a sequence of oxidative or reductive pulses that serve to convert the form of the redox-mediator into its oxidized or reduced form. In one aspect, the test subject can be one suspected of being afflicted with schizophrenia.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

EXAMPLE I

Materials and Methods

Chemicals

The following were purchased from Sigma-Aldrich: K2IrCl6 (IV), K3IrCl6 (III), glutathione (reduced, GSH), glutathione (oxidized, GSSG), ascorbic acid, uric acid, 5,5'-dithio-bis(2-nitrobenzoic acid) (DTNB), phosphate buffered saline (PBS). The water (>18 MΩ) used in this study was obtained from a Super Q water system (Millipore). A stock solution of 0.5 mM $K_2IrCl_6$(IV) was prepared in PBS (pH 7.4).

Serum Samples and Symptom Assessment

Recruitment of people to participate in a clinical study designed to collect blood samples occurred between May 2015 and August 2016. Blood samples were collected from the Maryland Psychiatric Research Center, University of Maryland School of Medicine. Two populations were recruited, people with a DSM-IV diagnosis of schizophrenia or schizoaffective disorder and a population of individuals without a major psychiatric diagnosis. All participants completed data collection procedures in a single 1-2 h study visit. Additionally, participants provided detailed clinical information. Blood samples (45 mL) were collected using 6 tubes of BD Vacutainers and centrifuged at 3000 rpm. The resulting supernatant was removed using disposable plastic 1 mL pipets. It was apportioned into 1 mL aliquots and stored at −80° C. in a freezer before analysis. To assay serum, the frozen serum was thawed at room temperature in the air for 30 min and then it was kept in an ice bath before the measurement.

The study to collect human serum from people with schizophrenia and healthy controls was approved by the University of Maryland School of Medicine IRB, and informed consent was obtained from all study participants prior to the research procedure.

A trained interviewer interviewed the people with schizophrenia to assess the Brief Psychiatric Rating Scale (BPRS), a clinical evaluation that rapidly provides measurement of clinical symptoms. The BPRS total score as well as five domain scores are calculated (positive, negative, anxiety/depression, hostility, and activation).

Research staff tasked with the collection of biological samples and protected health information have completed the requisite training and implemented standard procedures as required by The State of Maryland Department of Mental Health and Hygiene (DHMH) and the University of Maryland School of Medicine. Informed consent was obtained from each participant after reviewing relevant risks and benefits for the project. Successful completion of the Evaluation to Sign Consent was also required to demonstrate participant understanding of the voluntary nature of research, study tasks, and risks. The respective Institutional Review Boards for the University of Maryland and DHMH have approved this project and specified its conduct as having minimal risk to research participants.

Instrumentation

Electrochemical measurements (cyclic voltammetry (CV)) and chronocoulometry (CC)) were performed to measure the electrochemical signal (CHI420a electrochemical analyzer, CHInstruments, TX). For the electrochemical assay, a screen-printed carbon paste electrode (CHInstruments, TX) with carbon working and counter electrodes was used, and a Ag/AgCl reference electrode. The optical signal was recorded using a microplate reader (SperctraMax M2, Molecular Devices, CA).

Ir-Reducing Capacity Assay in Buffer

A stock solution of 10 mM $K_2IrCl_6$ and stock solutions of ascorbic acid (1 mM) and glutathione (GSH, 1 mM), oxidized glutathione (GSSG, 1 mM), trolox (1 mM) and uric acid (0.4 mM) were prepared in 0.1 M PBS (pH 7.4). A portion of each antioxidant stock solution was added into a 96 well-plate to generated 0 (blank), 20 µM, 40 µM, 60 µM, 80 µM, 100 µM antioxidant solutions. The 0.1 M PBS was added to each well to bring the volume to 95 µL. In each well, 5 µL of 10 mM K2IrCl6 (final concentration 0.5 mM) was added, mixed by pipetting and incubated for 30 min at room temperature. After that, the absorbance was measured at 488 nm using a microplate reader (optical measurement). For an electrochemical measurement, 100 µL of the mixture from each well was dropped onto a screen-printed electrode by covering all of the electrodes (working, counter, and reference electrodes). A constant potential of 0 V was applied to the electrode, and the charge was measured for 1 min using a chronocoulometry technique. All data shown in FIG. 1E and FIG. 2 were averaged from the measurements in quadruplicate, and the error bar indicates standard deviation (s.d.).

Ir-Reducing Capacity Assay in Filtered Serum

For a reducing capacity assay in filtered serum, microcon centrifugal filter device (EMD Millipore, MA) was used to remove biomacromolecues (MW>10 kDa) from serum. Serum was pipetted into the device and the assembly was placed in a centrifuge (Centrifuge 5415c, Eppendorf) and spun at 14 000 g. The filtrate was used for reducing capacity assay. A volume of 10 µL of filtered serum was added into a 96 well plate containing 85 µL of 0.1 M PBS, and then 5 µL of 10 mM K2IrCl6 was added to each well (this procedure results in a 10-fold dilution of the filtered serum). After adding the filtrate, buffer, and mediator, the solution was mixed by pipetting and incubated for 30 min at room temperature. The optical and electrochemical responses were measured as described above.

Ir-Reducing Capacity Assay in Serum

For a reducing capacity assay in serum, serum was first diluted 20-fold with 0.1 M PBS and 2 µL of diluted serum was added into a 96 well plate containing 93 µL of 0.1 M PBS, and then 5 µL of 10 mM $K_2IrCl_6$ solution was added to each well (this procedure results in an overall 1000-fold dilution of the filtered serum). After adding the solutions, mixing by pipetting and incubating for 30 min at room temperature, the optical response and electrochemical response were measured as described above. All data shown in FIG. 4 were averaged from the quadruplicate measurements and the error bar indicates standard deviation.

Cu-Reducing Capacity Assay

To compare the measured reducing capacity, a commercial reducing capacity assay was performed (cupric reducing antioxidant capacity (CUPRAC) assay, MAK187 from Sigma-Aldrich). To measure the reducing capacity of the sample, a portion of sample was added into a 96 well-plate and water was added to each well to bring the volume to 50 µL. In each well, 50 µL of Cu(II) working solution provided in an assay kit was added, mixed by pipetting and incubated for 30 min at room temperature. After incubation, the absorbance was measured at 570 nm using a microplate reader (optical measurement). All data shown in FIG. 3 were averaged from the triplicate measurements, and the error bar indicates standard deviation.

Measurement of Total Sulfhydryl Groups of Serum Samples

Total sulfhydryl groups of serum samples were assayed according to manufacturer's instructions (Quantification of Sulfhydryls, Uptima, Interchim). A dilution buffer (30 mM Tris HCl, 3 mM EDTA, pH 8.2) and DTNB working solution (3 mM in methanol) were prepared. As a standard for the free sulfhydryl group (—SH) assay, we prepared GSH solutions (0.1 mM to ~1 mM in dilution buffer). A volume of 20 µL of sample or standard solution, 75 µL of dilution buffer, 25 µL of DTNB reagent, and 400 µL of methanol were added into a microcentrifuge tube. After 5 min incubation, the mixture was centrifuged at 3000 g for 5 min at room temperature. The supernatant was transferred into a microplate. The optical absorbance was measured at 412 nm. All data shown in FIG. 4C were averaged from the quadruplicate measurements, and the error bar indicates standard deviation.

Statistical Analysis

The calculation of p-values in FIG. 4 was performed using a mixed design analysis of variance (SPANOVA). Receiver operating characteristic (ROC) curves for the antioxidant assays in FIG. 4E was determined utilizing OriginPro (OriginLab Corporation), and values were determined for area under curve (AUC) as shown in FIG. 4, the 95% confidence intervals, and the p-values. Relationships between reducing capacity and age or BPRS scores in FIG. 5 were assessed using Pearson's correlation coefficient. p-values in FIG. 5 were obtained from regression analysis (ANOVA).

Results

Assay Development

FIG. 1A depicts scheme for redox probing to access chemical information of oxidative stress. Top, chemical information relative to oxidative stress in the blood. Bottom, the redox-mediator ($K_2IrCl_6$, $Ir^{OX}$) is used to probe for reducing activities and reports this information through optical and electrochemical modalities.

Figure 1B:
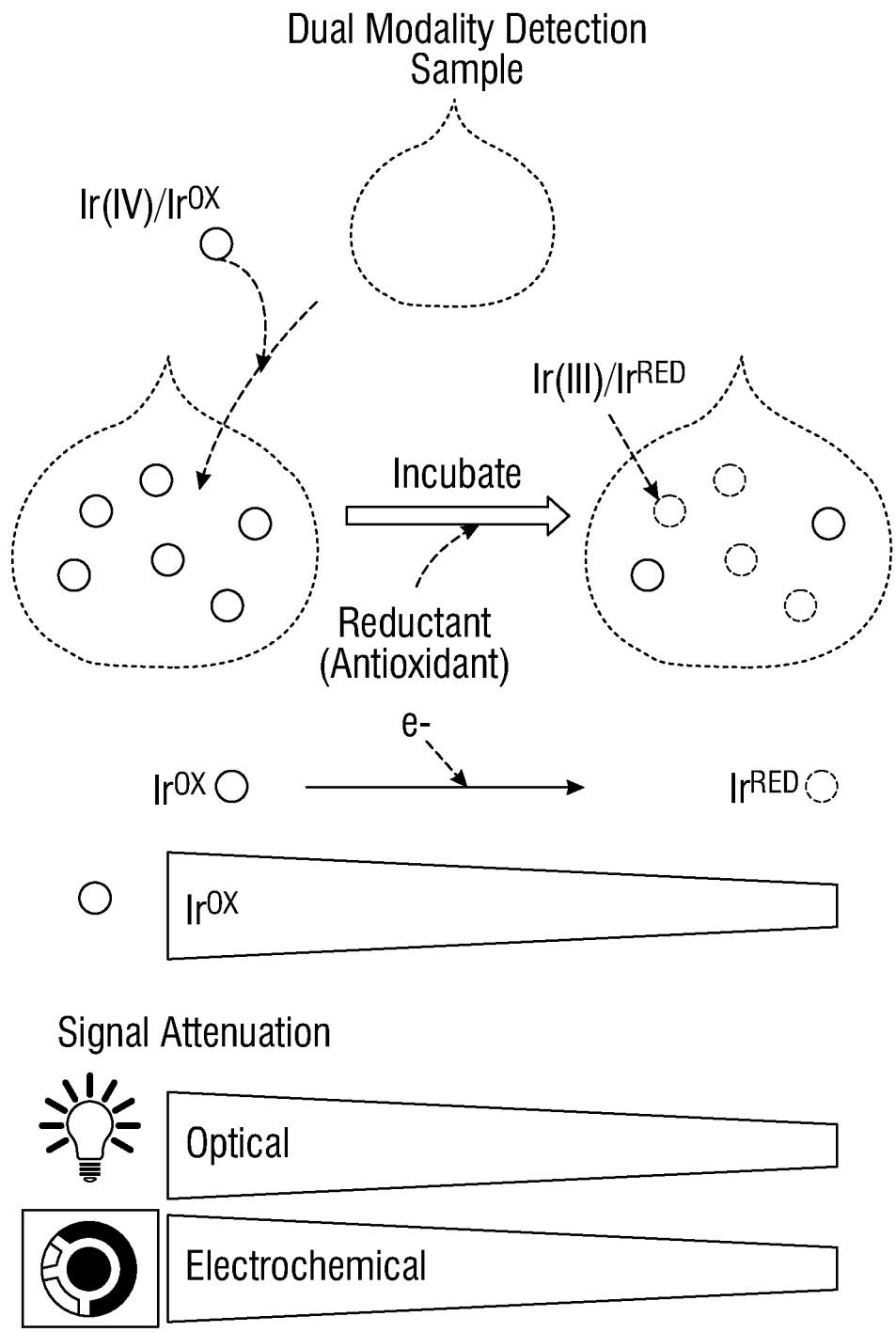

Qualitative Validation of Redox Probe $K_2IrCl_6$(IV), designated $Ir^{OX}$, was used to probe serum samples for redox information. As illustrated in FIG. 1B, $Ir^{OX}$ is a yellowish iridium(IV) complex that becomes colorless upon reduction to iridium(III), designated $Ir^{RED}$. As demonstrated in FIG. 1B, the basis of the method is that $Ir^{OX}$ is added to our serum sample to probe for reducing activities in the serum. Such reduction reactions can be detected by attenuations in either an optical signal associated with the loss of the yellow color or an electrical signal associated with a subsequent electrochemical titration of the remaining $Ir^{OX}$.

Figure 1C:
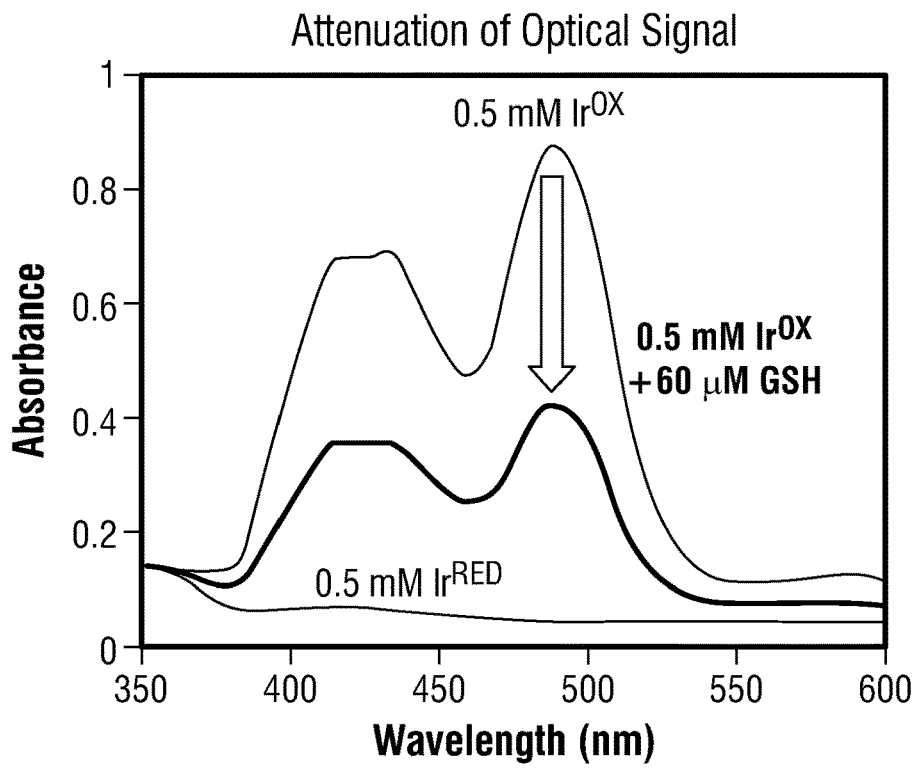

Attenuation of the optical signal is illustrated in FIG. 1C, which shows $Ir^{OX}$ (0.5 mM) has two strong absorbance peaks at 420 and 488 nm and these peaks are absent in the spectrum for $Ir^{RED}$. Addition of the biological reductant glutathione (GSH; 60 µM) to the $Ir^{OX}$ solution and incubation for 30 min was observed to attenuate this optical signal. Data shows attenuation is nearly complete after 30 min incubation although incubations may take place over extended periods of time, for example one or more hours, or for times less than 30 minutes.

Figure 1D:
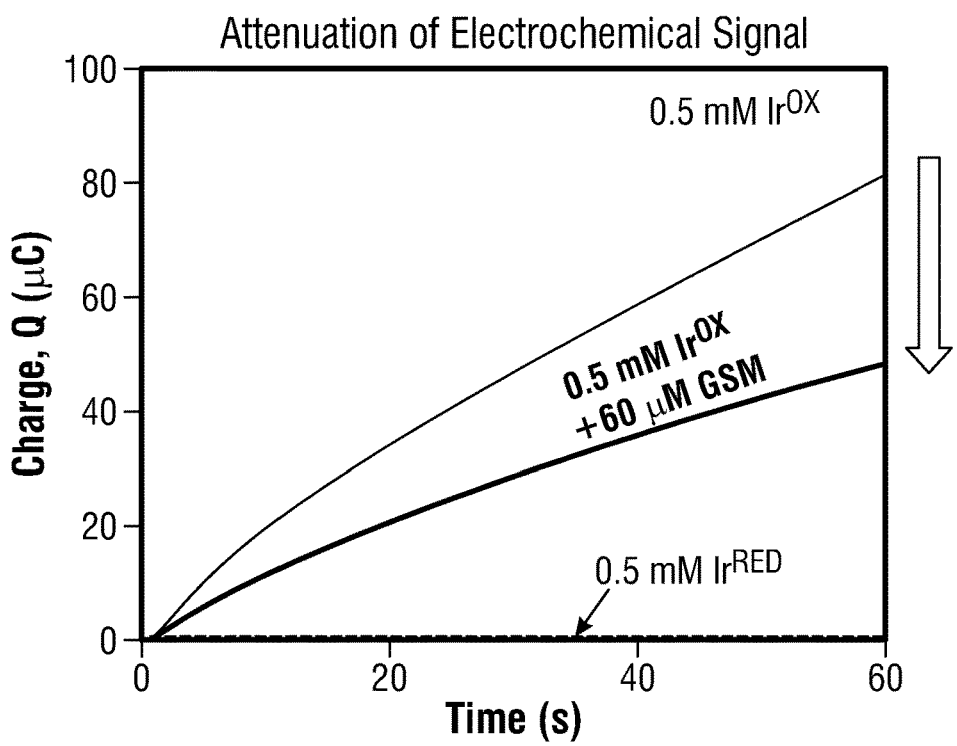

Attenuation of the electrochemical signal associated with the reduction of $Ir^{OX}$ is illustrated in FIG. 1D. For these measurements, a sample containing of $Ir^{OX}$ µL) was dropped onto the surface of a screen-printed 3 electrode system. Screen-printed electrodes were chosen because they are convenient, inexpensive, sensitive, and portable and thus are suitable for a point-of-care analysis.(44) Reduction of $Ir^{OX}$ is achieved using a constant imposed potential of 0 V vs Ag/AgCl. FIG. 1D shows the reductive charge transfer for $Ir^{OX}$ as measured by this chronocoulometry method. While solution containing the oxidized $Ir^{OX}$ shows a high reductive charge transfer after 1 min (Q≈80 mC), the solution containing the reduced $Ir^{RED}$ shows minimal charge transfer (Q≈1 mC). FIG. 1D shows that the addition of GSH to the $Ir^{OX}$ solution and incubation for 30 min leads to an attenuation of the reductive charge transfer.

Figure 1E:
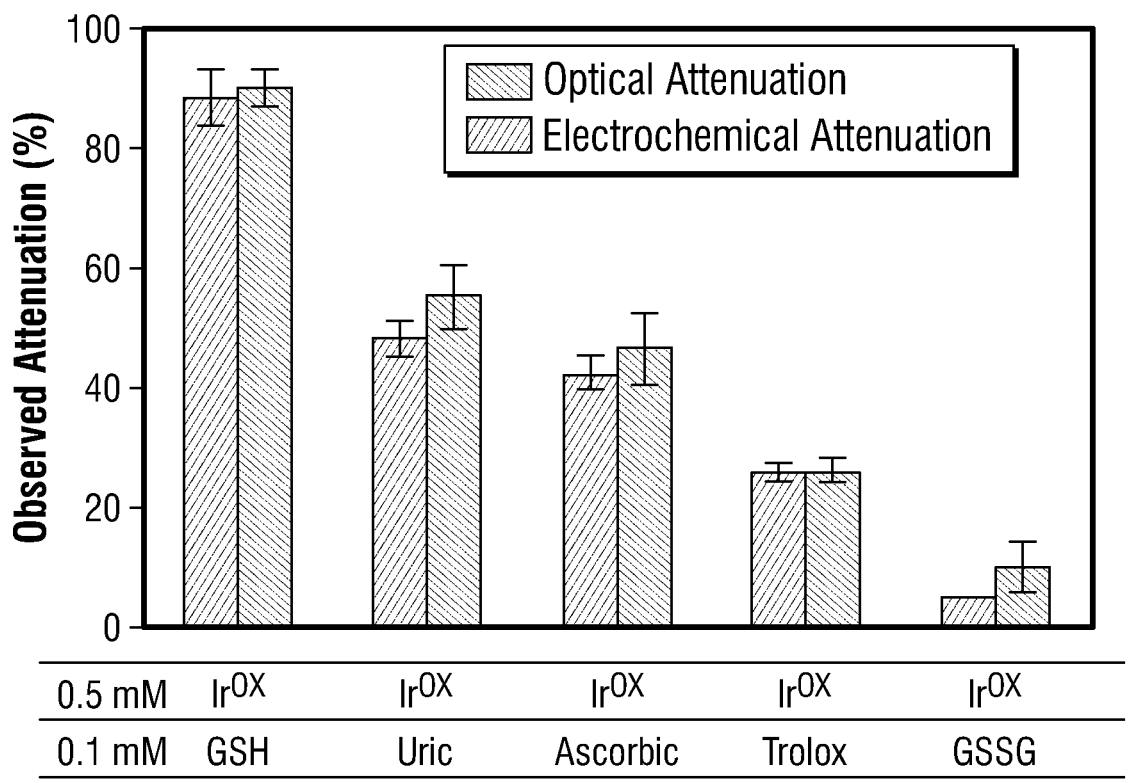

The equations in FIG. 1E show how attenuation of the optical signal (absorbance at 488 nm) and electrochemical signal (reductive charge transfer, Q, after 1 min at 0 V) was quantified. FIG. 1E also shows experimental results for the signal attenuation associated with various components. The reductant GSH shows the largest signal attenuation while the oxidized form of GSH, GSSG, shows the lowest signal attenuation (~6% of GSH attenuation). Uric acid and ascorbic acid are common reductants in blood and they showed intermediate signal attenuation. FIG. 1E also shows comparatively small signal attenuation for the commonly used antioxidant standard trolox.

In summary, FIG. 1 provides evidence that $Ir^{OX}$ can probe for redox information (e.g., the presence of reductants in a sample) and can report this information as an attenuation of signals through two separate modalities (optical and electrochemical). Importantly, the results in FIG. 1E show good agreement in the measured attenuations between these two modalities.

Quantitative Validation

Figure 2A:
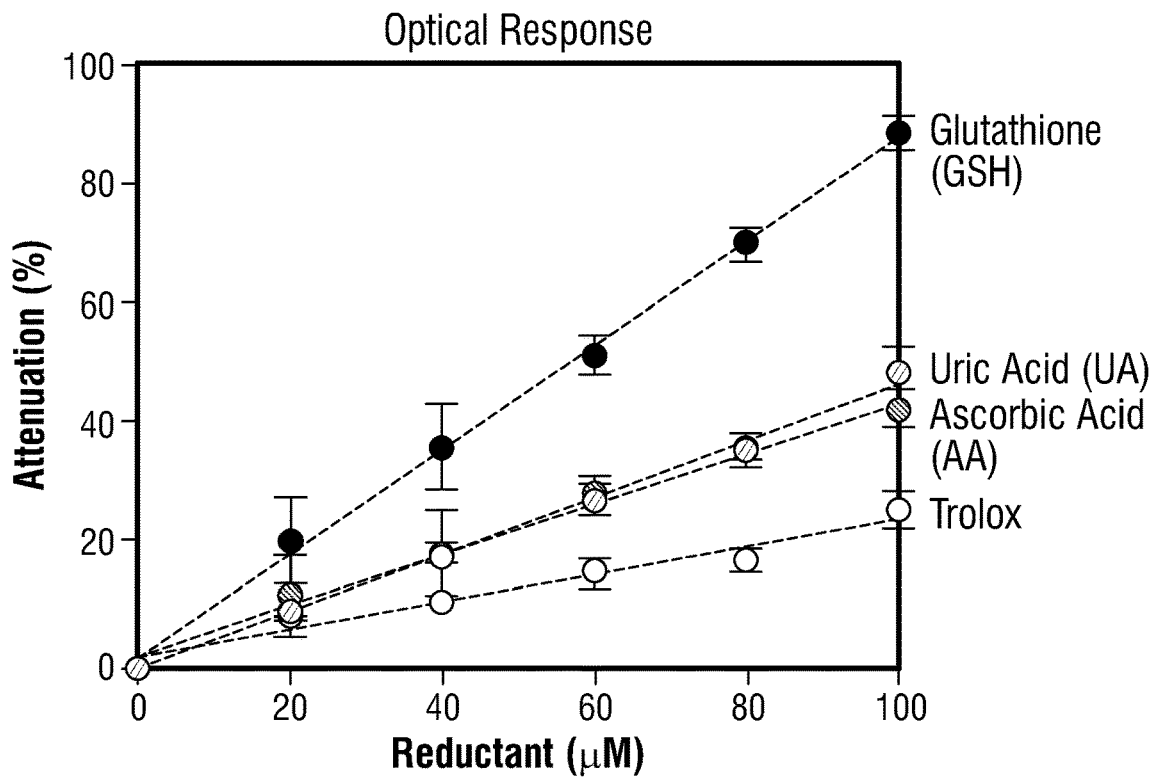
FIG. 2A-D shows quantitative validation of Ir-reducing assay.
Figure 2B:
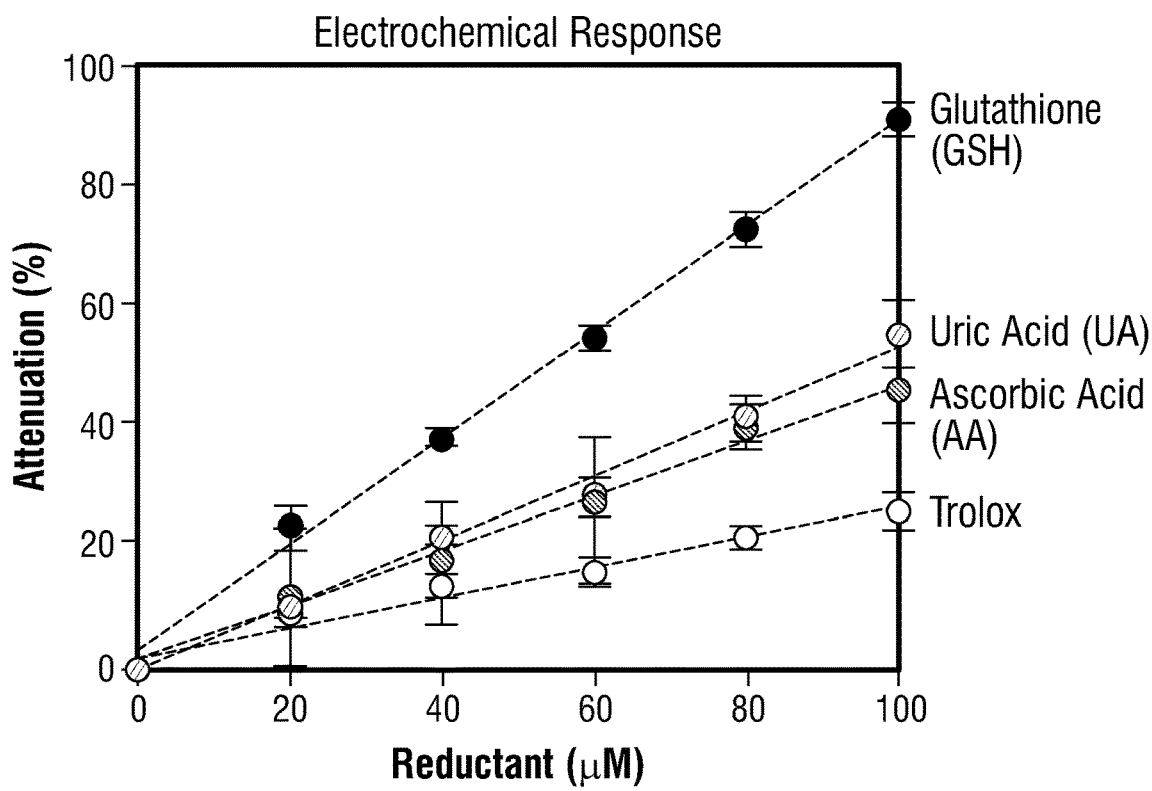
Figure 2C:
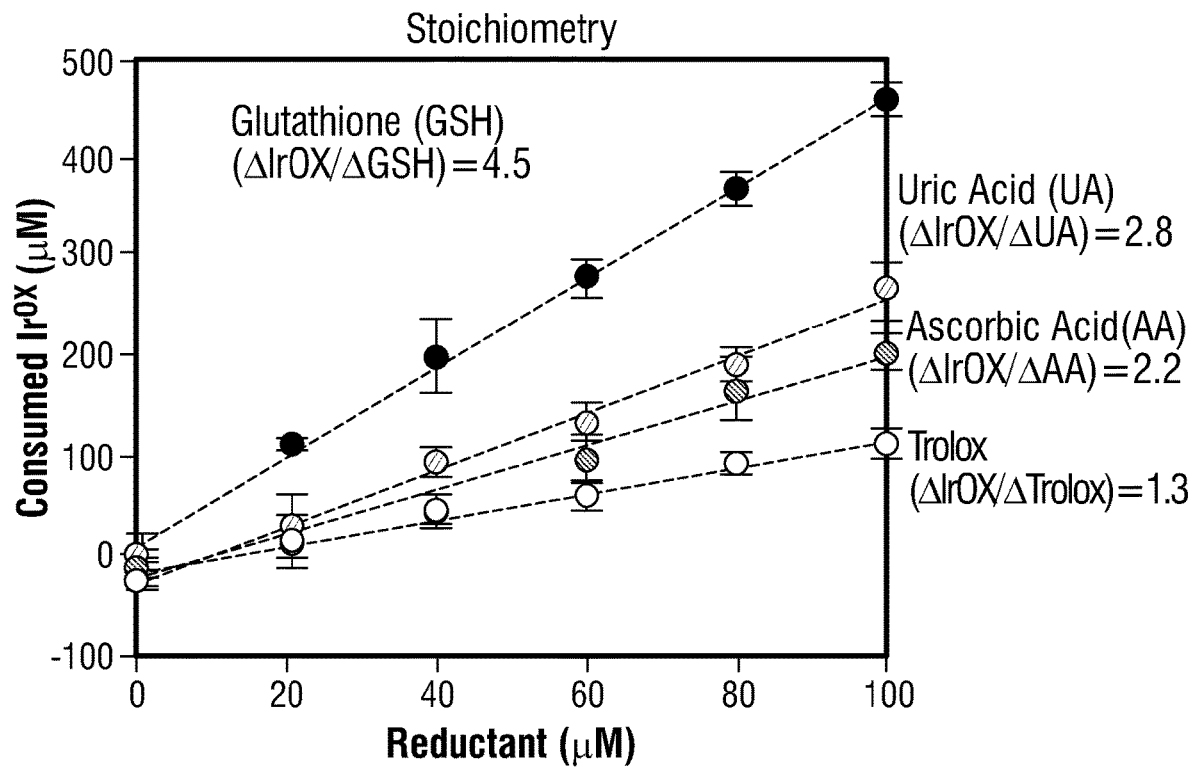

Intuitively, the reduction of $Ir^{OX}$ and attenuation of the signals are expected to be linearly dependent on the concentration of reductants in the sample. To test this expectation, $Ir^{OX}$ (0.5 mM) was mixed with varying concentrations of individual reductant, incubated for 30 min and measured signal attenuation. FIG. 2A shows that attenuation of the optical signal increased linearly with concentration for various reductants. Similarly, FIG. 2B shows attenuation of the electrochemical signal is linearly dependent on the reductant concentration. The slopes of the plots of FIGS. 2A-2B provide a measure of the reductant's ability to reduce $Ir^{OX}$ and this Ir-reducing capacity follows the trend GSH>>uric acid≈ascorbic acid>trolox for both the optical and electrochemical measurements. At higher reductant concentrations signal attenuation is complete and no longer sensitive to reductant levels.

Table 1 lists proposed reactions associated with the reduction of $Ir^{OX}$ by the various reductants. In the absence of $O_2$, it has been reported that the predominant $Ir^{Ox}$ oxidation of GSH is a 6 electron transfer to generate sulfonate ($GSO_3$—), while minor amounts of the oxidized disulfide (GSSG) are formed.(37, 45-47). Additional data shows GSH oxidation reactions that have been proposed to explain these stoichiometries. In the presence of $O_2$, experimental measurements showed the transfer of 4.2 electrons from GSH to $Ir^{OX}$ although no reactions were proposed.(37) This stoichiometric value of 4.2 is similar to the value of ~4.5 observed in FIG. 2C.(37). For the case of ascorbic acid (AA), Table 1 shows a 2 electron transfer to $Ir^{OX}$ was reported,(38) which is also consistent with the calculated value (~2.2) observed in FIG. 2C.

TABLE 1

Reaction stoichiometries with $Ir^{OX}$/Ir(IV)

| Reductants | Reaction Stoichiometry with $Ir^{OX}$/Ir(IV) | Ref |
|---|---|---|
| Glutathione (GSH) | 6 Ir(IV) + GSH + $3H_2O$ →6 Ir(III) + $GSO_3^-$ + $7H^+$ | 37 |
|  | 2 Ir(IV) + 2GSH → 2 Ir(III) + GSSG + $2H^+$ | 37 |

TABLE 1-continued

Reaction stoichiometries with $Ir^{OX}/Ir(IV)$

| Reductants | Reaction Stoichiometry with $Ir^{OX}/Ir(IV)$ | Ref |
|---|---|---|
| Ascorbate | 2 Ir(IV) + $H_2A$ → 2 Ir(III) + A + $2H^+$ | 38 |
| Cysteine | 6 Ir(IV) + $HSCH_2CHNH_3COO^-$ + $3H_2O$ → 6 Ir(III) + $HO_3SCH_2CHNH_2COO^-$ + $7H^+$ | 39, 45 |
| Quinols | 2 Ir(IV) + $H_2Q$ → 2 Ir(III) + Q + $2H^+$ | 73 |

Figure 2D:
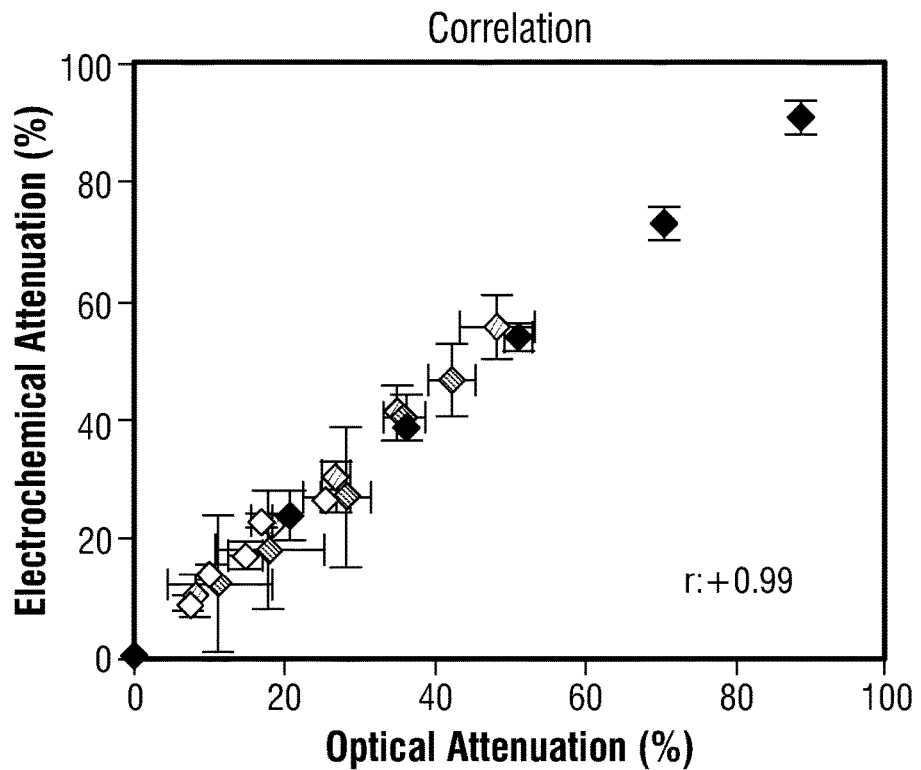

The correlation between the optical and electrochemical signals is shown in FIG. 2D, which shows a cross-plot of the attenuation percentages for the two modalities. As expected, there is a strong linear correlation in the attenuation of these two signals (correlation coefficient, r=0.995).

Figure 3A:
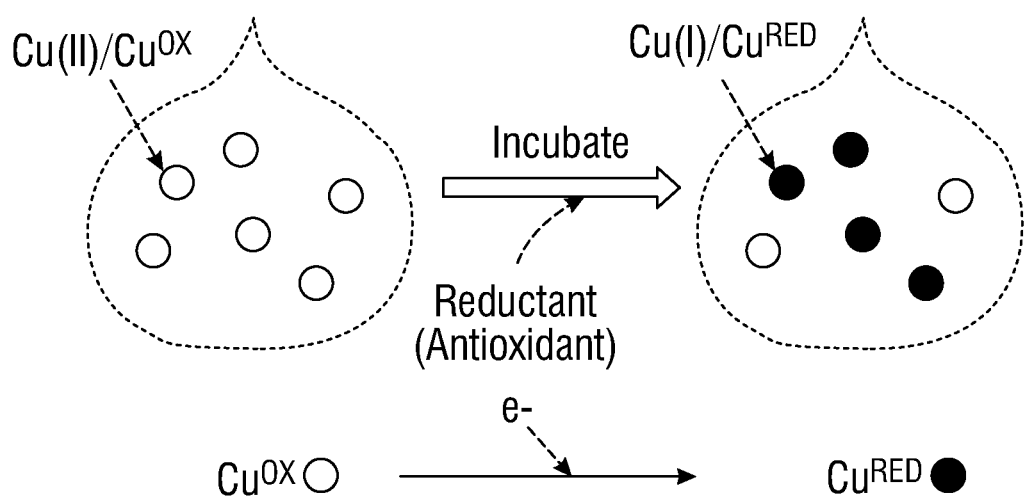
FIG. 3A-D demonstrates the comparison of Ir-reducing assay with other methods.

Several commercial methods have been developed to measure the global reducing capacity of a sample.(14, 15) These methods are based on the electron transfer from reductants in a sample to an added oxidant (probe), which causes a color change of the probe. Measurements were performed with one standard commercial method, the cupric reducing antioxidant capacity (CUPRAC) assay, to compare with the Ir-reduction method because the CUPRAC method has recently been used to measure total antioxidant activities in serum.(48) As shown in FIG. 3A, this commercial assay is based on a sample's ability to transfer electrons to a colorless Cu(II) (CuOX) solution to generate a purple-colored Cu(I) ($Cu^{RED}$). The color change associated with this reaction is monitored by measuring the absorbance at 570 nm. In contrast to the Ir-reducing assay where the signals are attenuated in the presence of reductant, the optical signals for the Cu-reducing assay increase in the presence of reductants.

Figure 3B:
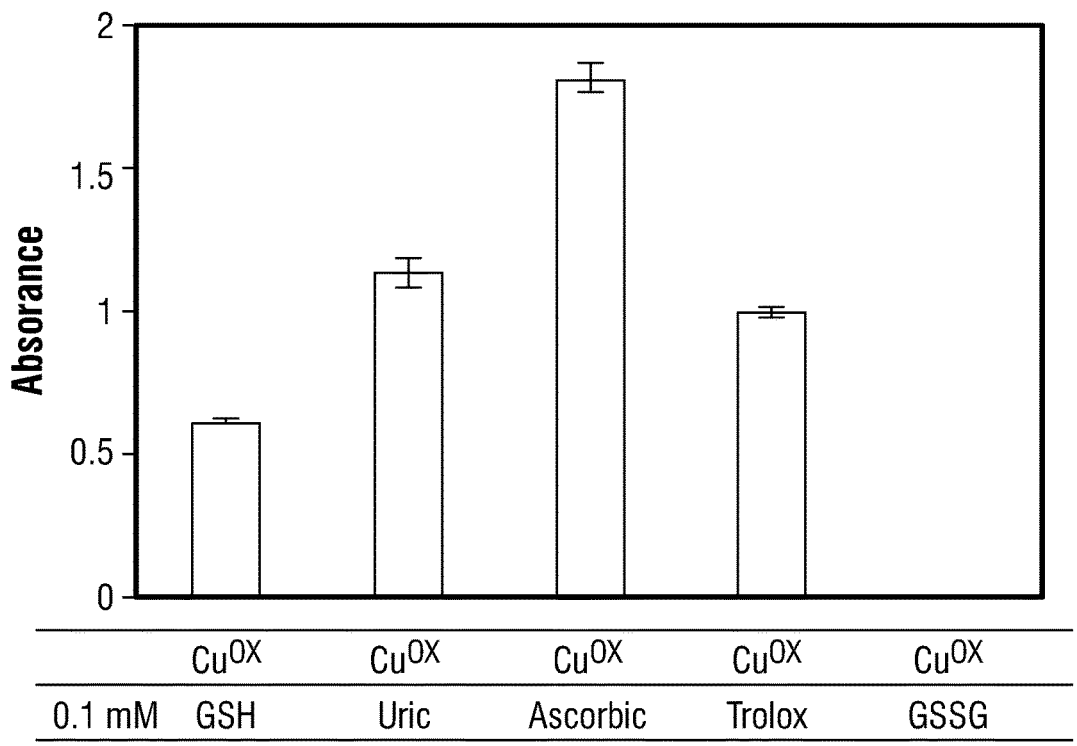

FIG. 3B shows the optical response (absorbance at 570 nm) when the $Cu^{OX}$ probe was mixed with various reductants and incubated for 30 min. As expected, the reduced glutathione (GSH) shows a positive response in this assay while the oxidized glutathione (GSSG) shows no response. FIG. 3B also shows the optical response of $Cu^{OX}$ varied depending on the reductant tested. For instance, ascorbic acid showed the highest response in this Cu-reduction assay.

Figure 3C:
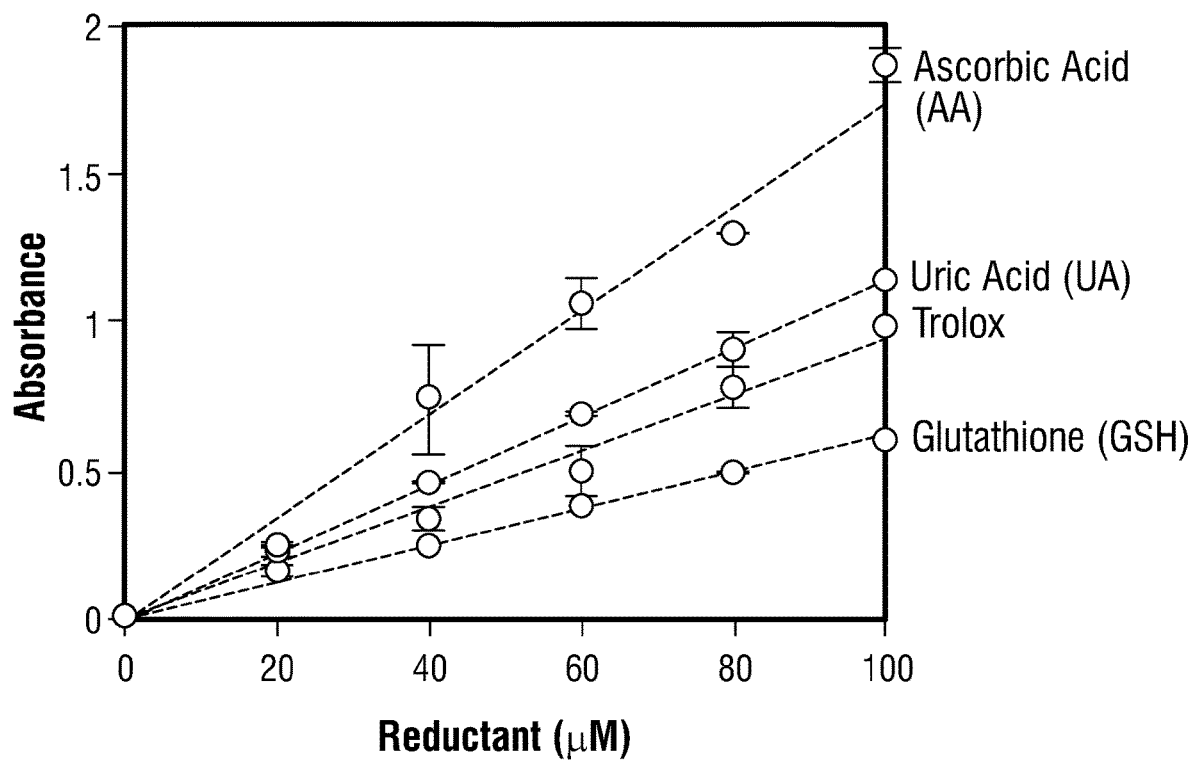

To quantitatively measure the reducing capacity of various reductants, the $Cu^{OX}$ probe was mixed with varying concentrations of an individual reductant, incubated for 30 min and measured the absorbance at 570 nm. FIG. 3C shows the optical response is proportional to the concentration of reductant being tested. As observed in FIG. 2, the slopes in the plot of FIG. 3C can be related to a reductant's reducing capacity. With the Cu-reduction assay, ascorbic acid has the highest reducing capacity and GSH has the lowest with the following trend: ascorbic acid>uric acid≈trolox>GSH. This trend is different than that observed with our Ir-reduction assay (FIG. 2). Thus, despite the fact that both assays are based on an electron-transfer reduction mechanism, the redox probes ($Ir^{OX}$ or $Cu^{OX}$) have differing sensitivities for accepting electrons from reductants.

In addition to the Cu-reduction assay, several other global assays have been developed to assess a sample's total antioxidant activities. These methods have been prominently applied to foods to provide a single-value measure of antioxidant activities for the purpose of understanding and comparing health beneficial properties of foods.(14, 15) These methods have also been extended to clinical samples in an effort to provide a quantitative measure useful for characterizing oxidative stress.(10, 49, 50) Typically, these assays are based on either a hydrogen atom transfer (HAT) or electron transfer (ET) mechanism.(14, 15, 48) HAT-based assays measure the ability of an antioxidant to scavenge free radicals by hydrogen donation and these methods include oxygen radical absorbance capacity (ORAC) and total radical-trapping antioxidant parameter (TRAP). In ET-based assays, the reducing capacity of reductants in a sample is measured by transferring an electron from the reductant to an oxidant probe that could be metals, carbonyls, and radicals.(15) The widely used ET-based assays are the trolox equivalent antioxidant capacity (TEAC) assay, the ferric ion reducing antioxidant power (FRAP) assay, the N,N-dimethyl-p-phenylenediamine (DMPD) assay, and the Cu-reduction (CUPRAC) assay of FIG. 3A.

Figure 3D:
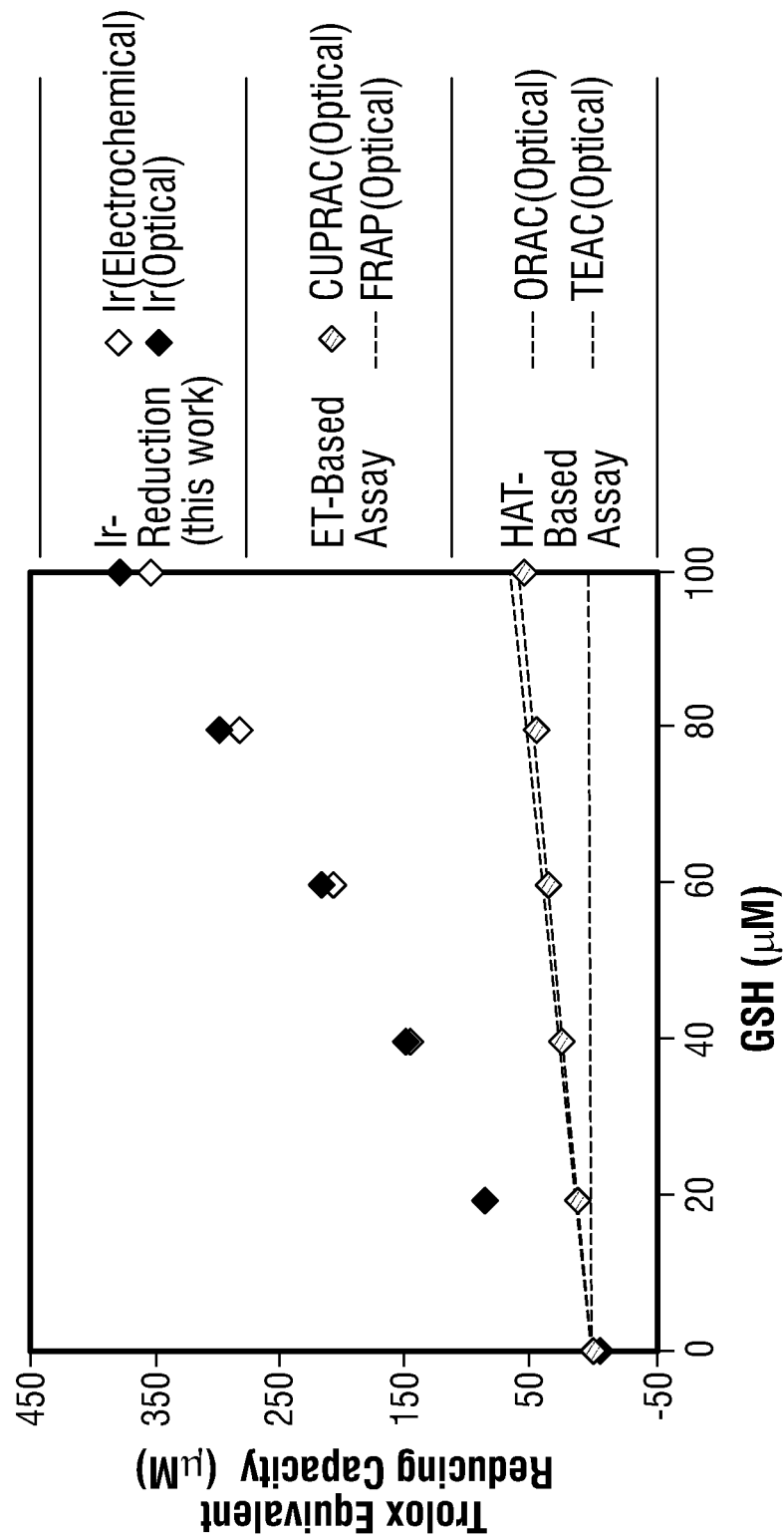

FIG. 3D shows the sensitivity of these various antioxidant assays to GSH. The Ir-reducing assay, using either the optical or electrochemical signals, shows comparatively high sensitivity to GSH compared to commercial Cu-reducing (CUPRAC) assay. Previous literature reports provided a comparison of the GSH-sensitivity for the ORAC, TEAC, and FRAP methods, and the best-fit lines from these studies are also shown in FIG. 3D.(49) These lines show that these standard methods have a comparatively low sensitivity for GSH, which is also consistent with reports that the FRAP assay has low sensitivity for detecting thiols in biological fluids.(15) One possible explanation for the greater sensitivity of the Ir-reducing assay for GSH is the more oxidative redox potential of the $Ir^{OX}$ mediator. Table 2 lists the redox potentials for each redox probe (i.e., oxidant) for the various reducing capacity assays. It is important to note however that thermodynamic explanations based on redox potentials may not be sufficient to explain differences in these methods because there can be significant kinetic barriers to electron transfer reactions. For instance, FIG. 3D shows the FRAP assay is unable to detect GSH despite the fact that the Fe(III) oxidant has a more oxidative redox potential compared to that for the Cu(II) oxidant of the CUPRAC method that is able to detect GSH.

TABLE 2

Redox potentials of various redox probes

| Assay | Redox potential | References |
|---|---|---|
| Ir-reduction Assay (Ir(IV)/Ir(III)) | +0.67 V vs Ag/AgCl | This work |
| CUPRAC assay (Cu(II)/Cu(I)) | +0.4 V vs Ag/AgCl | 48, 74 |
| FRAP assay (Fe(III)/Fe(II)) | +0.57 V vs Ag/AgCl | 48 |
| TEAC assay ($ABTS^{+*}$/ABTS) | +0.48 V vs Ag/AgCl | 75 |

In summary, the Ir-reducing assay uses $Ir^{OX}$ as an oxidative probe and reports information through either optical or electrochemical modalities. This method can detect reducing-activities from various reductants and is especially sensitive to GSH. GSH (and thiols in general) are believed to be important endogenous biological antioxidants yet these compounds are rather sluggish in transferring electrons and thus methods to detect biothiols often require special mediators (i.e., oxidative probes) or nanoparticles for their oxidation.(51-55) Not surprisingly, conventional antioxidant capacity assays developed for food applications are rather insensitive to GSH: phenolics and ascorbate (not thiols) are considered to be the important food antioxidants and thus special attention to GSH was not required for developing antioxidant measures for food analysis. For clinical applications, however, the high GSH-sensitivity of the Ir-reducing assay may be an especially important asset when probing serum samples for redox information on oxidative stress.

Clinical Testing

The underlying principles of this study are that (i) blood serum contains chemical information on oxidative stress, and (ii) this chemical information can be accessed by a global (i.e., chemically nonspecific) method of redox probing (10). Direct testing is currently impossible because of the ill-defined nature of oxidative stress, as well as uncertainties of which individual chemical species are the best markers of oxidative stress. Initial support for these principles is provided by an experiment in which serum was treated with an oxidative stressor (i.e., $H_2O_2$) and the change of its reducing capacity was measured. Supporting data shows that the addition of oxidative stressor (0.5 mM $H_2O_2$) decreased the reducing capacity of serum by up to 50%, which might be associated with the oxidation of amino acids by this stressor. (56-58) The focus of this study is a less direct, but potentially more important, test of these principles by evaluating correlations between measurements from the Ir-reduction assay and independent clinical measures of disease. For this, serum samples measurements from ten people diagnosed with schizophrenia and five healthy controls, were evaluated for possible correlations with clinical measures of disease (note: as in previous measurements, $O_2$ was not excluded during serum analysis). Growing evidence suggests oxidative stress plays an important role in schizophrenia.(43, 59-61) Importantly, no independent blood tests are currently widely used by clinicians to assist in diagnosing or evaluating the treatment response of schizophrenia.(62)

Comparison of Schizophrenia and Healthy Control Groups

Figure 4A:
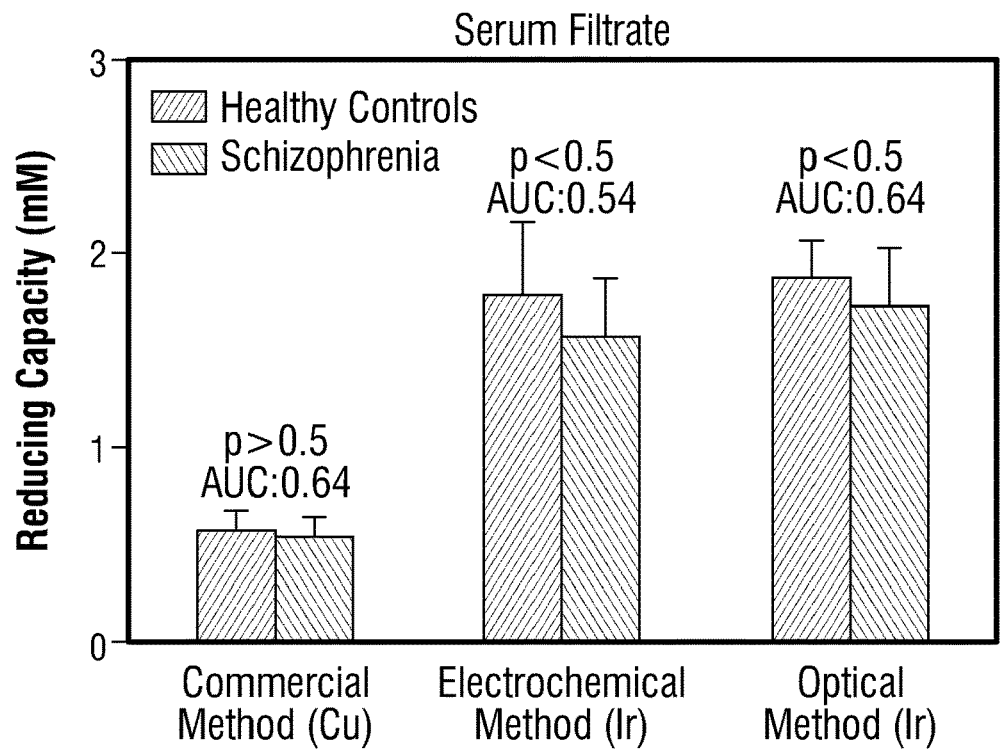
FIG. 4A-F shows clinical testing of reducing capacity of healthy control and schizophrenia groups.

In initial studies, proteins were removed from serum by filtering the serum using a centrifugal membrane filter (molecular weight cutoff=10 kDa), the filtrate was diluted 10-fold with phosphate buffered saline (PBS), and then the diluted filtrate was analysed by both the commercial Cu-reduction assay and the Ir-reduction assay (with both optical and electrochemical detection). Analysis of serum filtrates is expected to detect reducing contributions from low molecular weight components of serum such as ascorbic acid (AA), α-tocopherol, β-carotene, ubiquinol, glutathione (GSH), uric acid (UA), and bilirubin (49, 63). For comparison purposes, reducing capacity were normalized in terms of trolox equivalents, which is the common standard used for antioxidant reducing assays (15). FIG. 4A compares the serum filtrate's reducing capacity between the schizophrenia and control groups. The commercial Cu-reducing assay shows no differences between these serum filtrates (p=0.54), while the Ir-reducing assay shows serum filtrates from healthy controls have nonsignificant but higher average reducing capacity compared to those from the schizophrenia group (p=0.23).

Figure 4B:
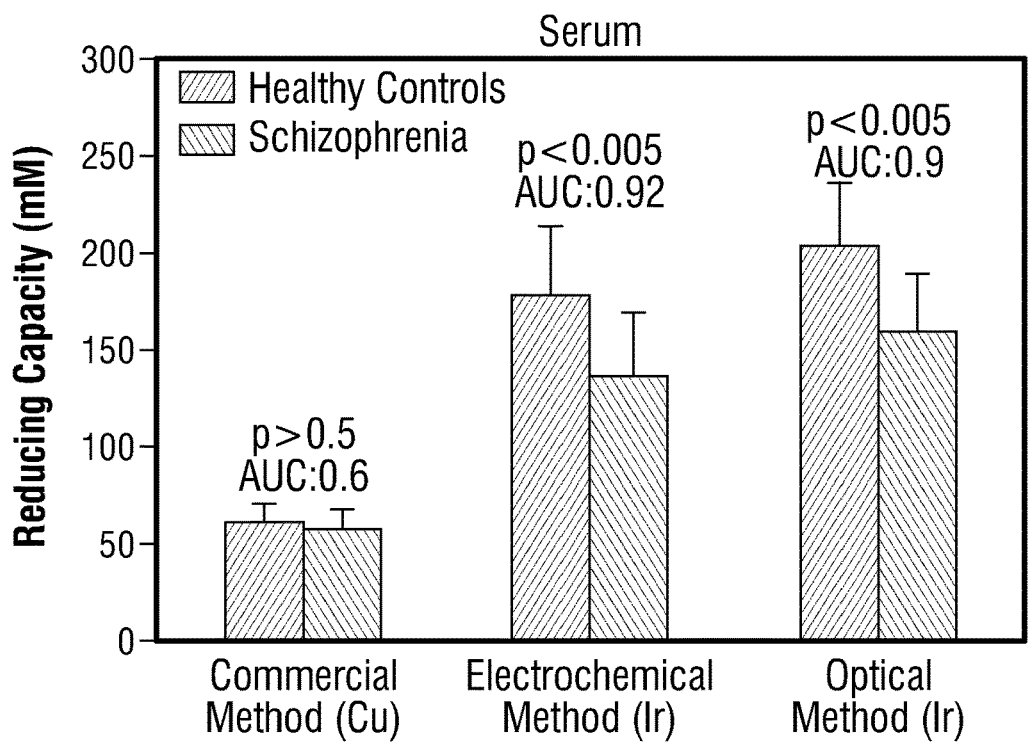

In addition to measuring serum filtrates, measurements were performed on serum after diluting the serum 1000-fold with PBS. Additional data shows that after 1000-fold dilution, the serum absorbance approaches that of the buffer background. FIG. 4B shows that when these serum samples were evaluated by the commercial Cu-reducing assay, no significant differences were observed between schizophrenia and control groups (p=0.63). In contrast, results from the Ir-reducing assay show considerably higher reducing capacities for serum from control group compared to serum from the schizophrenia group (p<0.005). Also, the Ir-reducing assay with serum (FIG. 4B) showed greater discriminating abilities compared to results with filtered serum (FIG. 4B).

Figure 4C:
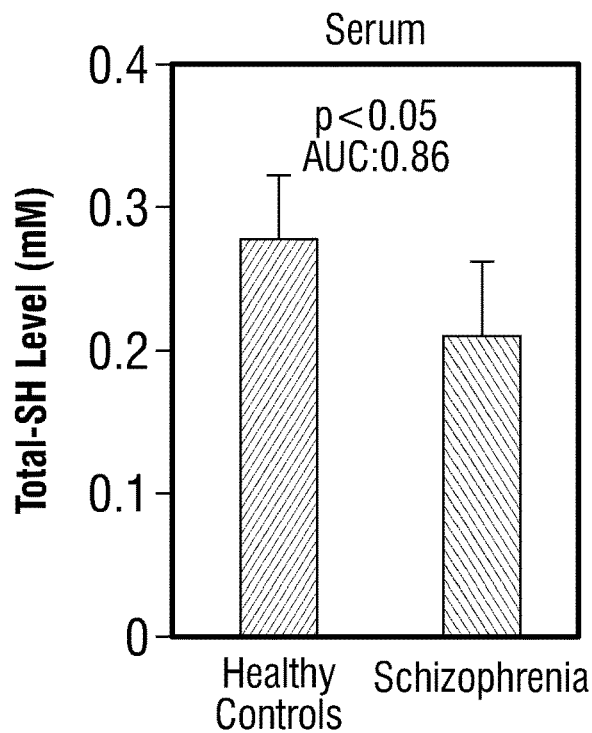
Figure 4D:
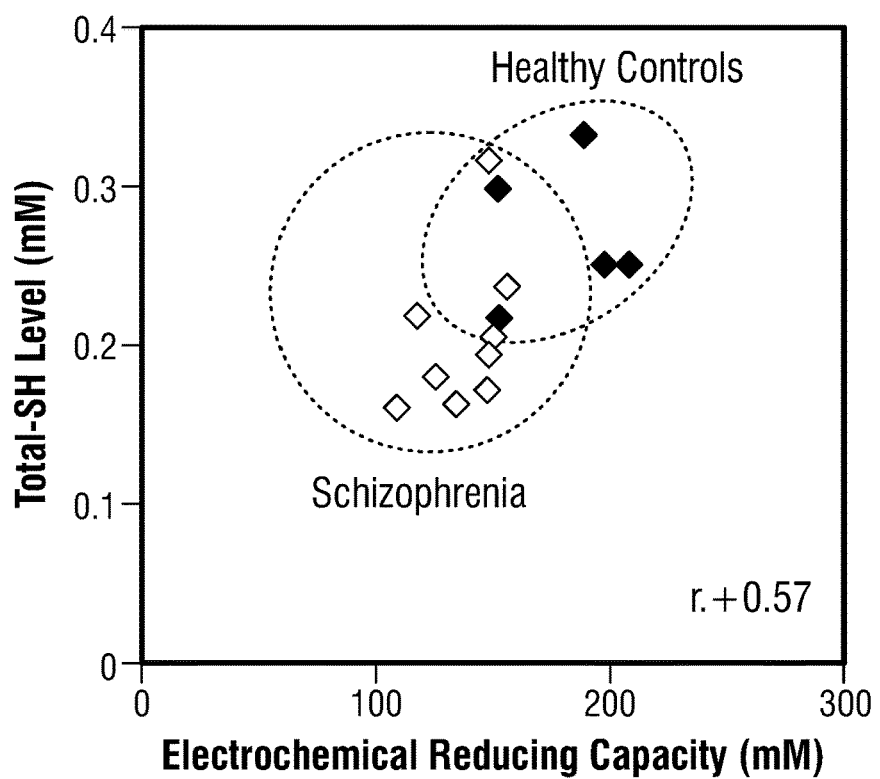

One possible explanation for the ability of the Ir-reducing assay to detect differences between the control and schizophrenia groups (compared to the commercial Cu-reducing assay), is the greater sensitivity of the Ir-reducing assay to sulfhydryl groups as observed in FIG. 3D. To evaluate this possibility, serum was assayed for total sulfhydryl groups (e.g., GSH and protein sulfhydryls) using a modified Ellman's method (64-66). FIG. 4C shows that the serum from control group has higher sulfhydryl values compared to serum from the schizophrenia group. FIG. 4D shows a modest positive correlation (N=15, r=+0.57, p=0.026) between total sulfhydryl group assay and the Ir-reducing capacity as measured electrochemically. This correlation indicates that the higher Ir-reducing capacity is modestly related to higher levels of total sulfhydryls. Thus, it appears that the higher sulfhydryl content in the serum from healthy controls is partially responsible for the higher measured Ir-reducing capacity.

Figure 4E:
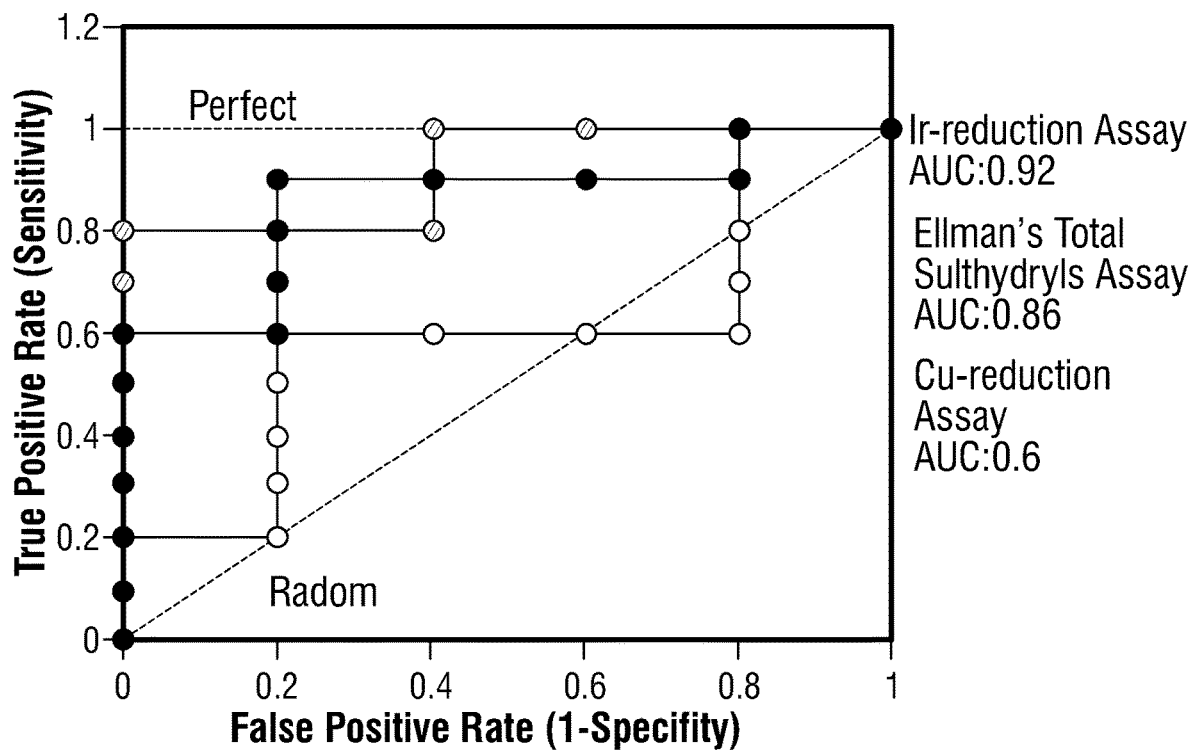

The clinical diagnostic performance of the assay was characterized using a receiver operating characteristic (ROC) curve analysis to determine if the measurements could discern the schizophrenia group from the healthy controls (62, 67, 68). In this method, the area under the ROC curve (AUC) for a perfect diagnostic test would be 1.0 while a random test would yield a value of 0.5. As shown in FIG. 4E, the calculated AUC values for the Ir-reducing capacity assay (with electrochemical detection) for serum was determined to be 0.92 (95% confidence interval (CI): 0.76-1.08; p=0.01), which compares to the value of 0.6 for the Cu-reducing serum assay (95% CI, 0.26-0.94; p=0.54) and 0.86 for the Ellman's free sulfhydryl group assay of serum (95% CI, 0.63-1.09; p=0.03). Thus, this analysis provides additional support that the Ir-reducing assay accesses clinically useful chemical information.

Figure 4F:
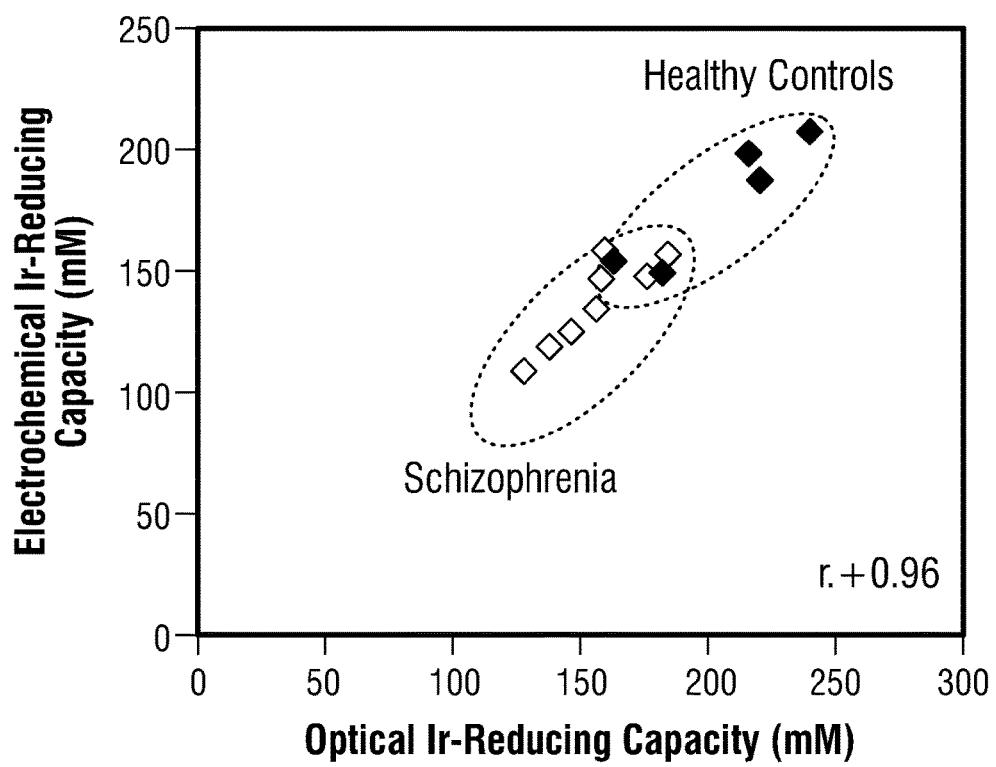

To further evaluate the Ir-reducing assay results for serum samples (FIG. 4B), a cross-plot between optical and electrochemical measurements was prepared. FIG. 4F shows a strong correlation between these two independent measurement modalities (N=15, r=+0.96) even in serum analysis.

In summary, the results in FIG. 4 indicate that the Ir-reducing capacity measurements with diluted serum can distinguish the schizophrenia group from the control group. The lower observed reducing activities in the serum of the schizophrenia group is consistent with suggestions that oxidative stress is linked to schizophrenia (43, 59).

Ir-Reducing Capacity Correlations to Age and Disease Severity

The original free radical theory of aging hypothesized that aging results from cumulative damage associated with free radicals (69) and several studies have established correlations between age and various markers of oxidative damage (70, 71). If the Ir-reducing assay accesses important chemical information on oxidative stress, then one would expect correlations between age and Ir-reducing capacity. FIG. 5A-B shows inverse correlations between age and Ir-reducing capacity for the individual schizophrenia and control groups as well as for the overall population of both groups. Importantly, the boxed regions in FIG. 5B show that if an age cutoff of 50 years is applied to the data, the Ir-reducing assay can fully distinguish the schizophrenia group from healthy controls (p<0.05). Specifically, the two overlapping data points in FIG. 4F are for the oldest healthy controls.

Potentially, the Ir-reducing assay is accessing chemical information on oxidative stress that is related to the severity of symptoms in people with schizophrenia, and thus correlations might be expected between Ir-reduction capacity and independent clinical measures of symptom severity. The most widely used scale for measuring psychotic symptoms is the brief psychiatric rating scale (BPRS), which is based on a clinician's interview and observations of the patient (72). The BPRS scale considers several items, and higher scores indicate more severe symptoms. FIG. 5A shows statistical information for correlations between these composite psychotic symptoms and Ir-reducing capacity for the 10 persons in the schizophrenia group. As expected, most symptoms show a negative correlation between symptom severity and Ir-reduction capacity (i.e., greater symptom severity is correlated to greater oxidative stress). The strongest correlation was observed between anxiety/depression and Ir-reducing capacity (N=10, r=−0.74, p=0.015) in FIG. 5C, while the weakest correlation was observed for the negative symptom. The positive symptom (psychosis) also showed a high correlation between symptom severity and Ir-reducing capacity (N=10, r=−0.64, p=0.048) in FIG. 5D.

In summary, the initial clinical results in FIG. 5 further support a conclusion that the Ir-reduction assay accesses chemical information that could be useful for understanding and managing diseases that are believed to be linked to oxidative stress.

Clinicians routinely assess patients using simple physical measurements that provide global information in a timely manner (e.g., measurements of temperature, pulse and blood pressure). Blood contains valuable chemical information on a patient's health, and blood tests are routinely used to access specific chemical information (e.g., of individual metabolites, antibodies, or biomarkers). For the case of oxidative stress, a focus on specific (vs global) chemical information may be less helpful to clinicians for two reasons. First, acquiring specific chemical information often requires specialized instrumentation in centralized laboratories which generally means this chemical information is not available in a timely manner. Second, for the case of oxidative stress, it is not clear what specific chemical information is most relevant. As a result, for diseases such as schizophrenia, clinicians do not even use chemical information for diagnosis or assessment. A method is disclosed to access global chemical information on oxidative stress. While the development of this method was guided by chemical/medical intuition (e.g., a requirement for high GSH sensitivities), this method is not chemically specific but more broadly probes for redox-information. Clinical evaluations indicate this method may access valuable chemical information while the speed and simplicity of the method suggests this information could be available at the point-of-care.

In addition to providing timely chemical information at the point-of-care, it is believed there is a second potential advantage of the Ir-reducing assay. If this measurement proves to be a reliable indicator to assist in the diagnosis and assessment of symptom severity, then these measurements could become an important investigational tool. For instance, this measurement could provide clinical researchers with a readily measurable objective target to assess therapeutic interventions. Alternatively, experimental research to unravel the chemical basis of the Ir-reduction signal could discover clues of the molecular mechanisms important in oxidative stress. Such a "reverse engineering" of the Ir-reduction signal can provide a complementary approach to alternative, instrument-intensive discovery approaches (i.e., -omic based methods). In summary, the Ir-reduction assay described herein is important because it provides simple near-real-time access to important global chemical information in serum.

Described herein is a simple, rapid, and robust method to probe serum for chemical information relevant to oxidative stress. This iridium-reducing assay uses $K_2IrCl_6$ ($Ir^{OX}$) as a redox-mediator to detect the serum's reducing activities and can detect this activity by independent optical and electrochemical modalities. Compared to alternative global reducing assays, the Ir-reducing assay has a high sensitivity to GSH which is an especially important attribute for probing serum for information on oxidative stress. Initial clinical evaluations show that the Ir-reducing assay can discern a schizophrenia group (N=10) from healthy controls (N=5, p<0.005) and showed an inverse correlation between reducing activities and the severity of the anxiety/depression (N=10, r=−0.74, p=0.015) and psychosis symptoms (N=10, r=−0.64, p=0.048) for the schizophrenia group. In conclusion, the Ir-reducing assay accesses global chemical information on oxidative stress with the sensitivity, speed, and simplicity required for point-of-care measurement. This chemical measurement can complement other global physical measures (e.g., temperature and blood pressure) used routinely for the rapid clinical evaluation of a patient's status.

EXAMPLE II

Spectroelectrochemical (SEC) Assay.

Figure 6:
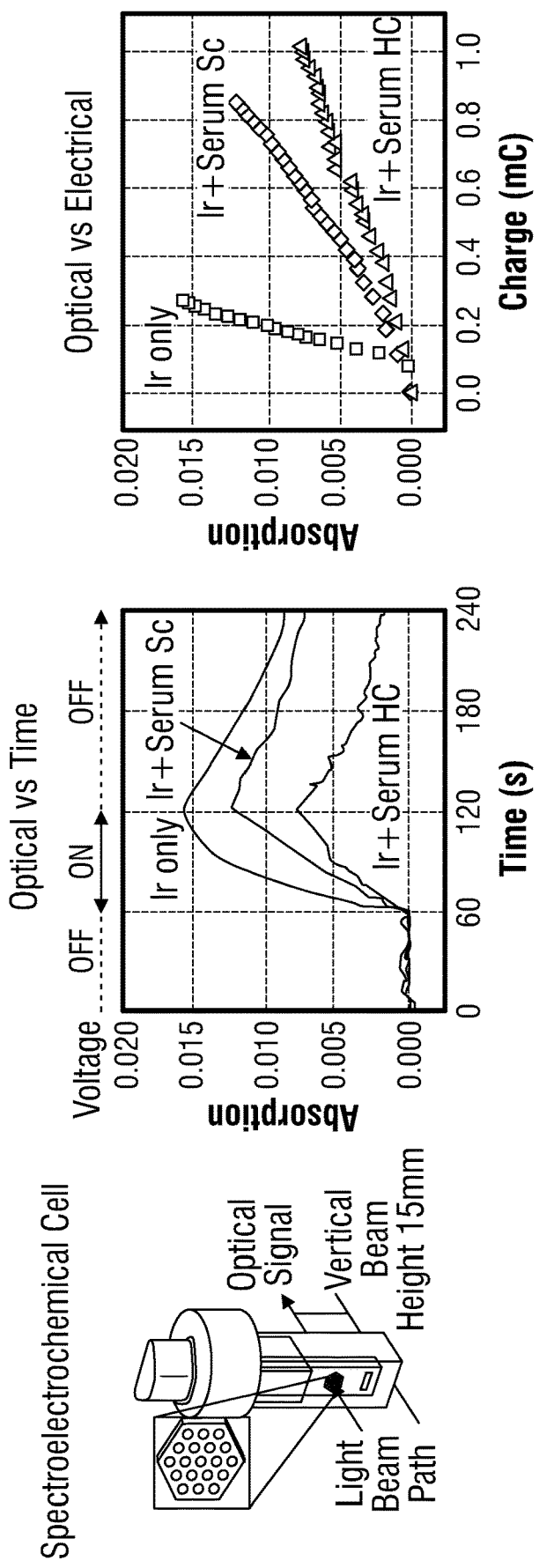
FIG. 6 depicts a spectroelectochemical (SEC) assay. The SEC-cell allows dynamic measurements through two modalities. Initial experiments demonstrate that when the oxidative voltage in "ON" the color of the oxidized Ir ($Ir^{OX}$) emerges and this optical signal is attenuated when serum components react with the $Ir^{OX}$. Signal attenuation is greater for the healthy control (HC) versus the oxidatively stressed schizophrenia person (SC).

End-point assays are expanded to a dynamic measurement and from one single measurement modality to the simultaneous measurement of two modalities (optical and electrical) and these will enhance the power of the assay as an industry-desired platform. Specifically, the SEC cell of FIG. 6 will be used. FIG. 6 shows preliminary results with 10× diluted serum from the most-oxidatively stressed schizophrenia person (Sc) and a least-oxidatively stressed healthy control (HC). The central plot in FIG. 6 shows that: (i) when the electrode voltage is switched "ON", $Ir^{RED}$ is oxidized and a yellow color associated with oxidized Ir ($Ir^{OX}$) emerges, and (ii) when the voltage is switched "OFF" the optical signal (yellow color) decays. When serum is included with $Ir^{RED}$, the emergence of color is attenuated during the "ON" step and the signal decay is more rapid during the "OFF" step: both differences occur because components in the serum react with the oxidized Ir. At the right in FIG. 3 is a cross-plot between the optical signal (yellow color) and electrical signal (number of electrons transferred to oxidize Ir). Both plots show significant discrimination between the most-oxidatively stressed Sc and a least-oxidatively stressed HC. These results show that SEC is a powerful tool to reverse engineer serum samples to discover oxidative stress (OxSt) signatures that discriminate the schizophrenia and control groups, and better correlate to clinical measures of symptom severity.

The SEC-cell allows dynamic measurements through 2 modalities. Initial experiments show that when the oxidative voltage is "ON" the color of the oxidized Ir emerges; this optical signal is attenuated when serum components react with the Ir. Signal attenuation is greater for the healthy control (HC) vs the oxidatively stressed schizophrenia person (Sc).

OxSt measurements can be combined for end-point or dynamic measurements with clinical data from the schizophrenia and control groups to identify confounding influences. For instance, studies have identified a strong negative correlation between age and OxSt, and when an age cut-off was applied, it was possible to completely discriminate the schizophrenia and control groups. A General Additive Model (GAM) may be implemented to test for confounding and modifying factors and evaluate the statistical significance ($p<0.05$) of these interactions.

EXAMPLE III

Figure 7A:
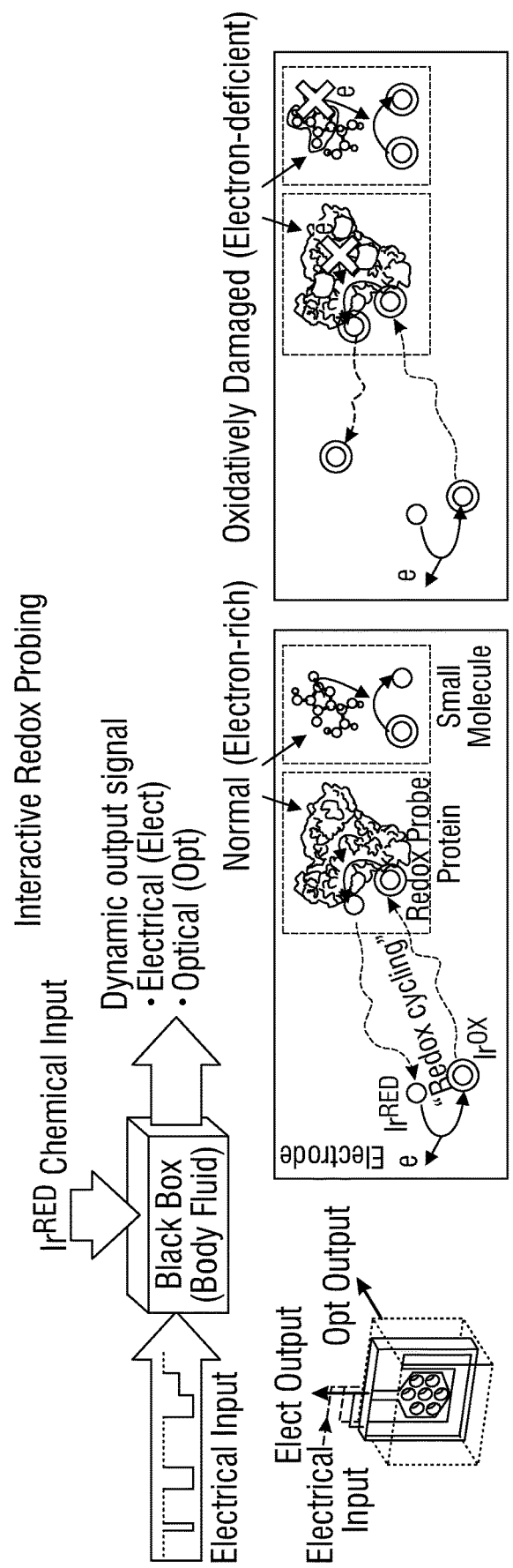
FIG. 7A illustrates our signal processing approach in which a sample (e.g., diluted serum) is actively probed for redox-based chemical information using tailored chemical and electrical signals.

FIG. 7A illustrates a signal processing approach in which a sample (e.g., diluted serum) is actively probed for redox-based chemical information using tailored chemical and electrical signals. The chemical input added to the sample is an iridium-based redox-mediator that can exchange electrons with a wide range of components (e.g., glutathione) and report electron exchange by redox-state-dependent optical and electrical outputs (Kim, E. et al. Redox Probing for Chemical Information of Oxidative Stress. Anal. Chem. 89, 1583-1592 (2016)) The electrical input is a sequence of oxidative voltage pulses that serve to convert the inert reduced form of iridium (designated $Ir^{RED}$) into its oxidized form (designated $Ir^{OX}$) which diffuses into the sample in "search" of electron-rich components. Such redox-probing can globally access information of reactive oxidants (e.g., free radicals) and the redox-state of protective reductants, as well as discerning oxidative damage (e.g., oxidized proteins). The output optical and electrical responses are measured simultaneously using a perforated electrode in a spectroelectrochemical cell illustrated in FIG. 7A.

Figure 7B:
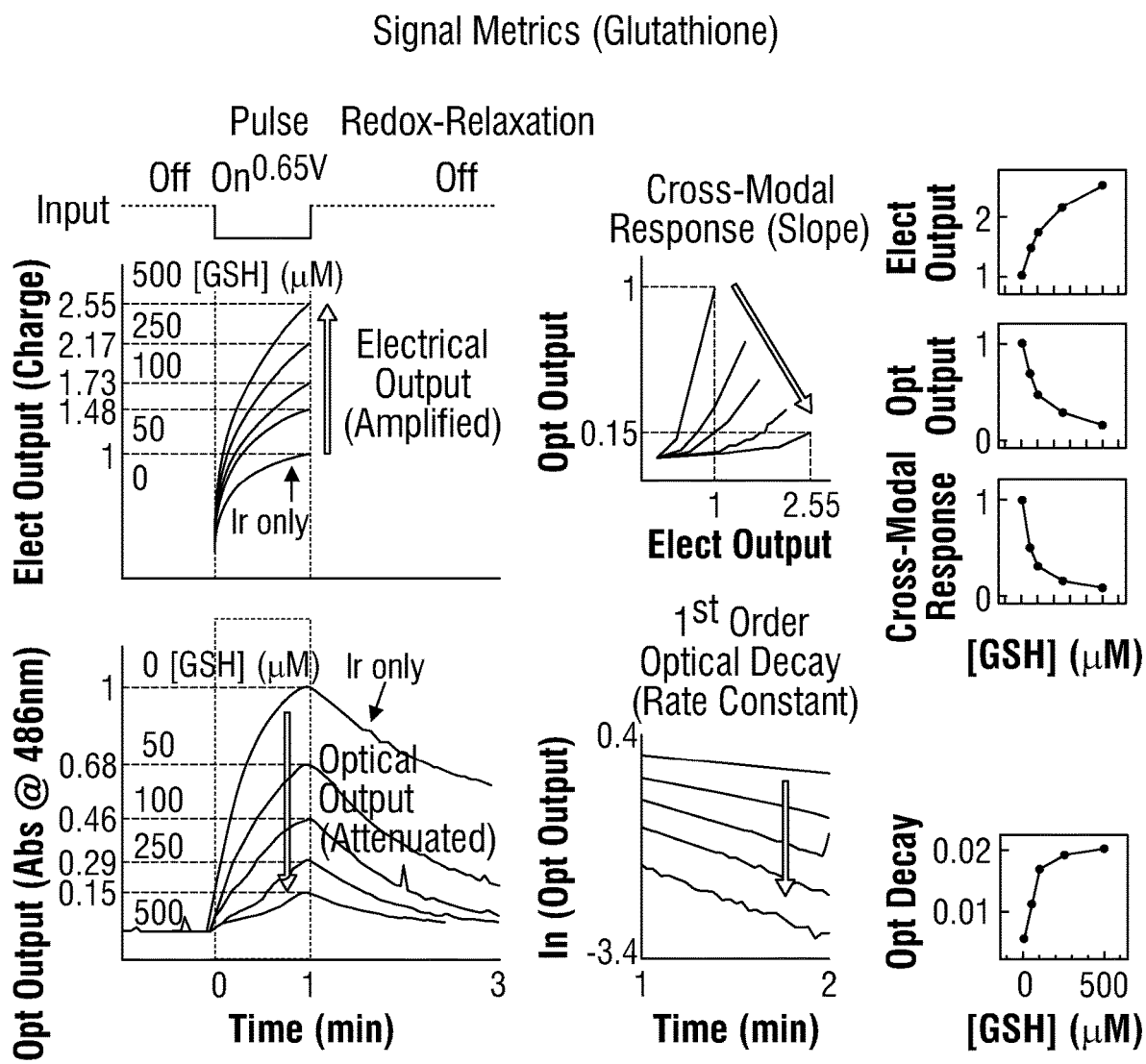
FIG. 7B shows three quantitative signal metrics determined from this on-pulse: the electrical output (charge transferred; $Q=\int idt$), optical output (absorbance 488 nm) and a cross-modal response between the optical and electrical output signals (quantified as a slope). To initiate probing, an oxidative input pulse of +0.65 V was imposed for 1 min to generate $Ir^{OX}$ and then the electrical and optical responses were monitored over time. A fourth signal metric is measured during the off period and this metric is the first order rate constant for decay in the optical signal.

The measurement approach is illustrated using buffered solutions of the physiological antioxidant glutathione (GSH) with added $Ir^{RED}$. To initiate probing, an oxidative input pulse of +0.65 V was imposed for 1 min to generate $Ir^{OX}$ and then the electrical and optical responses were monitored over time (FIG. 7B). Electron exchange between $Ir^{OX}$ and this antioxidant enables redox-cycling which amplifies the electrical current and attenuates the optical absorbance. FIG. 7B shows three quantitative signal metrics determined from this on-pulse: the electrical output (charge transferred; $Q=\int idt$), optical output (absorbance 488 nm) and a cross-modal response between the optical and electrical output signals (quantified as a slope). After the 1 min oxidative pulse the input voltage is turned off allowing a redox-relaxation of the optical signal which decays more rapidly in the presence of GSH. The first-order rate constant for this decay in optical absorbance serves as a fourth signal metric (FIG. 7B). As expected, the results show a systematic variation in the four signal metrics with variations in GSH concentration.

Figure 7C:
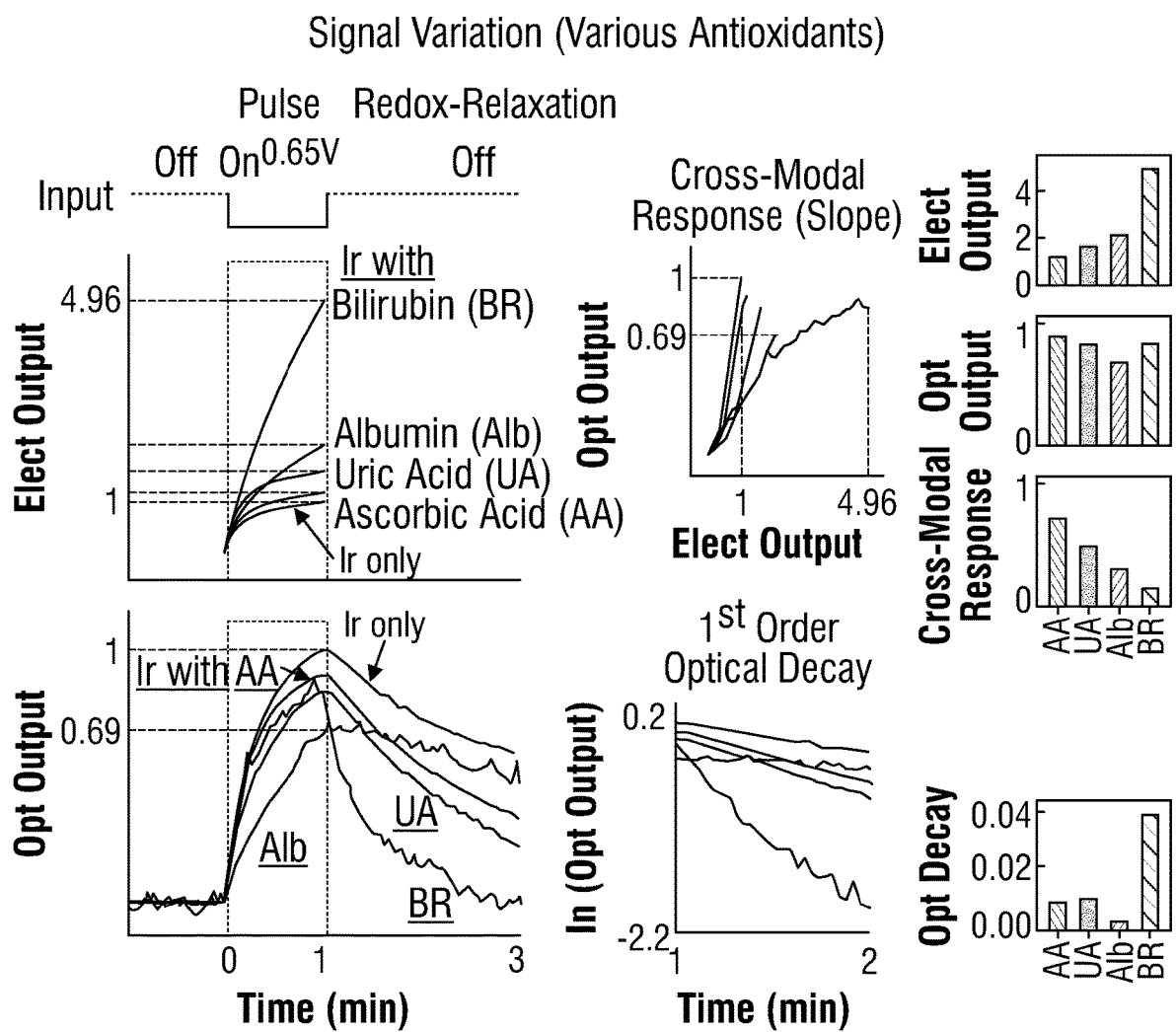
FIG. 7C demonstrates that when buffered solutions were prepared with individual chemical components that are expected to contribute antioxidant activity to serum (concentrations were selected to approximate serum concentrations), complex signal outputs for these components where observed and these differences are reflected in differences in the observed signal metrics.

In a second control study, buffered solutions were prepared with individual chemical components that are expected to contribute antioxidant activity to serum (concentrations were selected to approximate serum concentrations). FIG. 7C shows more complex signal outputs for these components and these differences are reflected in differences in the observed signal metrics. In particular, the reactive bilirubin shows large amplification in the electrical output and a rapid decay in the optical signal, while the more slowly reacting albumin shows less amplification in the electrical signal and a slowly decaying optical signal. These observations illustrate that the spectroelectrochemical measurement and the four quantitative signal metrics possess molecule-dependent and concentration-dependent information.

To demonstrate the potential of the signal processing approach, schizophrenia was used as an initial clinical example. Schizophrenia is a complex poorly understood disease that lacks simple objective measures and thus blood tests are currently unavailable to assist clinicians in diagnosis, assessment and management. Emerging research indicates oxidative stress is strongly linked to schizophrenia. Accordingly, active probing of a serum sample for redox-based chemical information may reveal valuable global signatures.

Figure 8A:
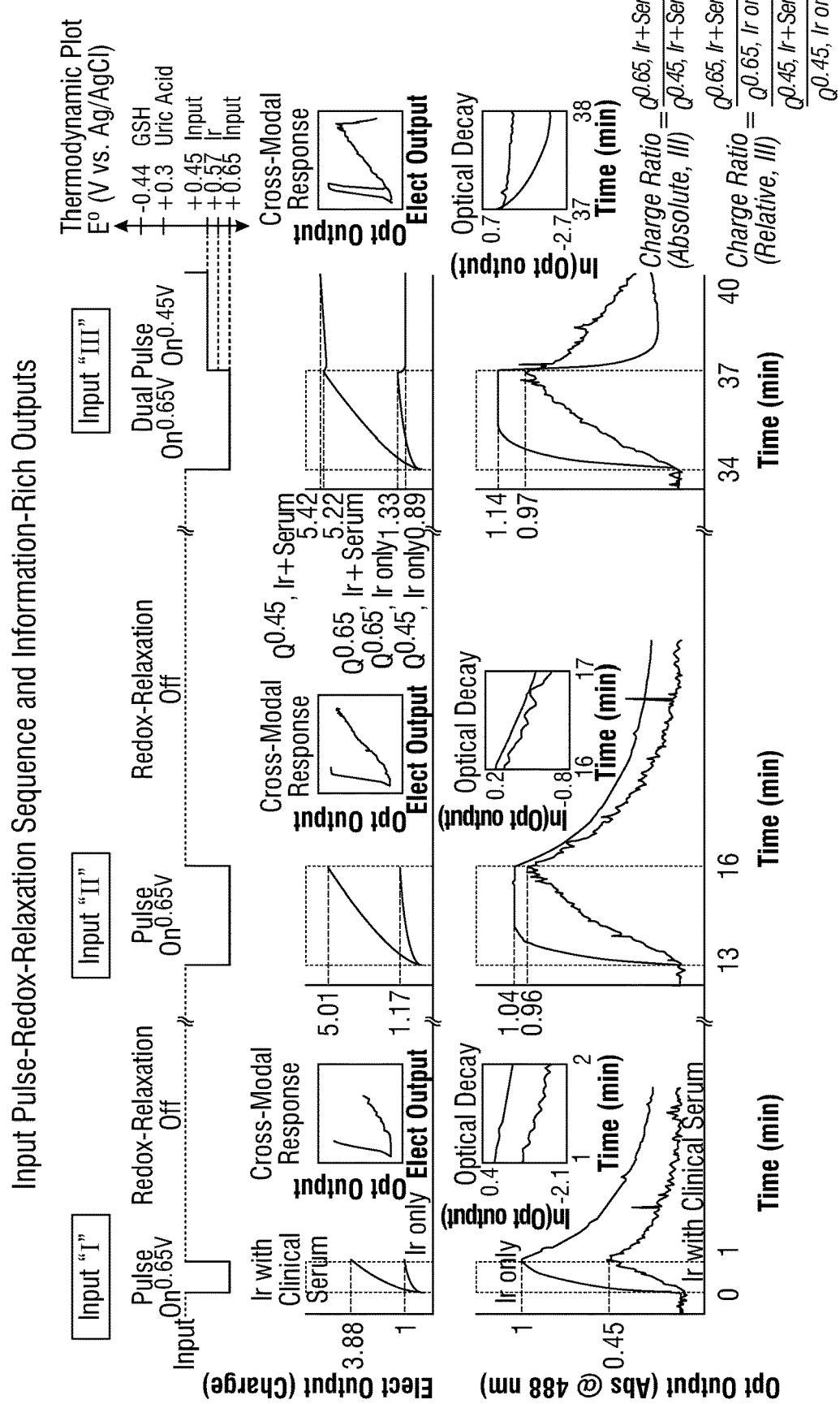
FIG. 8A shows representative results for a buffered Ir solution and a solution with 10-fold diluted serum when a three pulse-redox-relaxation sequence was selected.

To probe clinical serum samples, a three pulse-redox-relaxation sequence was selected and FIG. 8A shows representative results for a buffered Ir solution and a solution with 10-fold diluted serum. The first and second pulses, designated I and II, are short (1 and 3 min) oxidative voltage (+0.65 V) pulses that are each followed by an off-voltage that allows decay of the optical signal. The final pulse input, III, is a 3 min oxidative voltage (+0.65 V) immediately stepped down to a less oxidative voltage (+0.45 V) for 3 min. These two voltages bracket the redox potential of Ir ($E°=+0.57$ V vs. Ag/AgCl). For the control Ir solution during pulse input III: (i) the +0.65 V step oxidizes $Ir^{RED}$ to generate $Ir^{OX}$ and results in an oxidative electrical current and a growing optical signal; and (ii) the +0.45 V step reduces $Ir^{OX}$ back to $Ir^{RED}$ leading to a reversal in currents and a rapid decay in optical signal. For the sample (Ir plus diluted serum) during pulse input III, FIG. 8A shows that the step to +0.45 V leads to a short reversal of currents followed by a resumption in oxidation. Presumably serum components are being electrochemically oxidized at +0.45 V as suggested by the thermodynamic plot at the right in FIG. 8A. Input III leads to two additional signal metrics based on ratios of the charge transfer observed during the +0.65 V pulse and the +0.45 V pulse (these metrics are illustrated at the lower right in FIG. 8A).

Using the above input pulse sequence, 15 clinical serum samples were probed: 10 from persons diagnosed with schizophrenia and 5 from healthy controls. Each sample was measured in triplicate and each measurement results in 14 quantitative metrics (4 each for input pulses I and II, and 6 for pulse input III). These signal metrics were then compared to independent measurements of serum composition and clinical assessments.

One expectation is an internal consistency among signal metrics and this is illustrated by the two plots in FIG. 8A which show high correlations between signal metrics generated during the first pulse. A second expectation, is that the signals generated should be related to the underlying chemical composition of the serum. Each of the 15 serum samples tested was independently analyzed by a central laboratory for several chemical components. Albumin and uric acid are the macromolecule and small molecule antioxidants present in serum at the highest concentrations (Cao, G. & Prior, R. L. Comparison of different analytical methods for assessing total antioxidant capacity of human serum. Clinical Chemistry 44), and FIG. 8C shows correlations between these serum components and two signal metrics. Ascorbic acid is also expected to be an important antioxidant in serum, but less significant correlations are observed with our signal metrics presumably because of the comparatively lower serum ascorbic acid concentrations. In summary, these correlations indicate that the signals generated from this pulse-redox-relaxation sequence are internally consistent and are accessing relevant chemical information in serum.

Figure 8D:
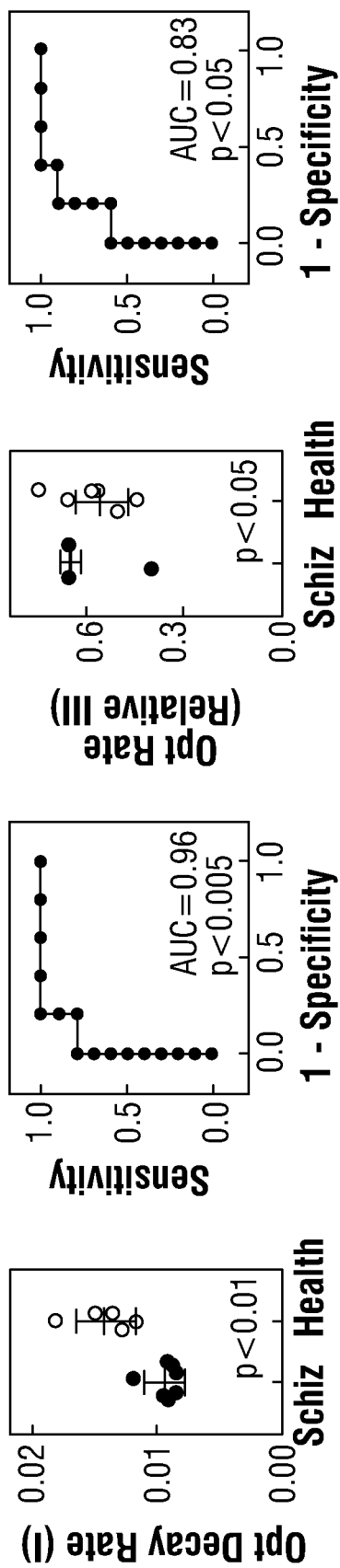
FIG. 8D shows the decay in the optical signal after the initial 1 min pulse input I shows statistically significant differences between the schizophrenia and control groups. A second metric, of the relative charge ratio during the final input pulse III, also shows statistically significant discriminating capabilities.
Figure 8D:
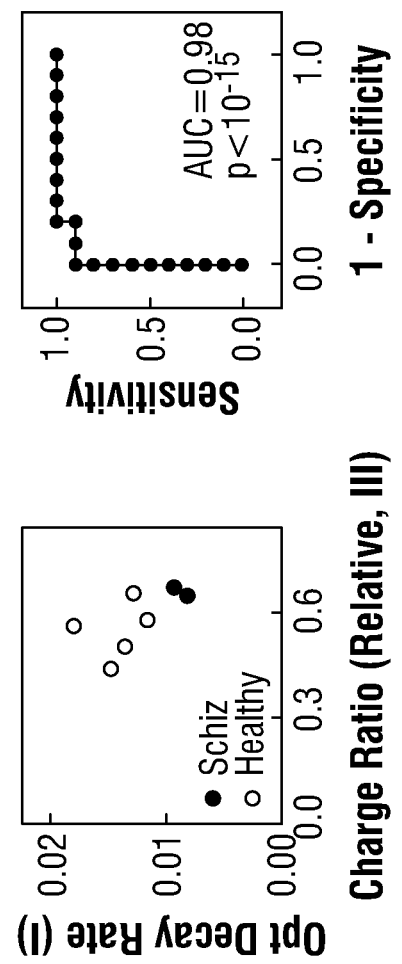

Finally, it was assessed whether the objective redox-based chemical features that are characterized by our signal metrics can be correlated to clinical assessments (i.e., a diagnosis of schizophrenia) that resulted from subjective clinical evaluations. FIG. 8D shows the decay in the optical signal after the initial 1 min pulse input I shows statistically significant differences between the schizophrenia and control groups. A second metric, of the relative charge ratio during the final input pulse III, also shows statistically significant discriminating capabilities.

REFERENCES

1. Valko, M.; Leibfritz, D.; Moncol, J.; Cronin, M. T. D.; Mazur, M.; Telser, J. Int. J. Biochem. Cell Biol. 2007, 39, 44-84 DOI: 10.1016/j.biocel.2006.07.001
2. Pohanka, M. Curr. Med. Chem. 2014, 21, 356-364
3. Finkel, T.; Holbrook, N. J. Nature 2000, 408, 239-247
4. Emiliani, F. E.; Sedlak, T. W.; Sawa, A. Curr. Opin Psychiatry 2014, 27, 185-190
5. Kohen, R.; Nyska, A. Toxicol. Pathol. 2002, 30, 620-650
6. Elmarakby, A. A.; Sullivan, J. C. Cardiovasc. Ther. 2012, 30, 49-59
7. Schieber, M.; Chandel; Navdeep, S. Curr. Biol. 2014, 24, R453-R462
8. Baraibar, M. A.; Ladouce, R.; Friguet, B. J. Proteomics 2013, 92, 63-70
9. Fedorova, M.; Bollineni, R. C.; Hoffmann, R. Mass Spectrom. Rev. 2014, 33, 79-97
10. Ghiselli, A.; Serafini, M.; Natella, F.; Scaccini, C. Free Radical Biol. Med. 2000, 29, 1106-1114
11. Kim, E.; Liu, Y.; Ben-Yoav, H.; Winkler, T. E.; Yan, K.; Shi, X.; Shen, J.; Kelly, D. L.; Ghodssi, R.; Bentley, W. E.; Payne, G. F. Adv. Healthcare Mater. 2016, 5, 2595-2616
12. Woodford, F. P.; Whitehead, T. P. Ann. Clin. Biochem. 1998, 35, 48-56
13. Serafini, M.; Del Rio, D. Redox Rep. 2004, 9, 145-152
14. Huang, D.; Ou, B.; Prior, R. L. J. Agric. Food Chem. 2005, 53, 1841-1856
15. Prior, R. L.; Wu, X.; Schaich, K. J. Agric. Food Chem. 2005, 53, 4290-4302
16. Erel, O. Clin. Biochem. 2004, 37, 112-119
17. Apel, K.; Hirt, H. Annu. Rev. Plant Biol. 2004, 55, 373-399
18. Nathan, C.; Cunningham-Bussel, A. Nat. Rev. Immunol. 2013, 13, 349-361
19. Moura, F. A.; de Andrade, K. Q.; dos Santos, J. C. F.; Araújo, O. R. P.; Goulart, M. O. F. Redox Biol. 2015, 6, 617-639
20. Reuter, S.; Gupta, S. C.; Chaturvedi, M. M.; Aggarwal, B. B. Free Radical Biol. Med. 2010, 49, 1603-1616 DOI: 10.1016/j.freeradbiomed.2010.09.006
21. Sies, H. Redox Biol. 2015, 4, 180-183
22. Jones, D. P. Antioxid. Redox Signaling 2006, 8, 1865-1879
23. Jones, D. P. American Journal of Physiology—Cell Physiology 2008, 295, C849
24. Schafer, F. Q.; Buettner, G. R. Free Radical Biol. Med. 2001, 30, 1191-1212
25. Levonen, A.-L.; Hill, B. G.; Kansanen, E.; Zhang, J.; Darley-Usmar, V. M. Free Radical Biol. Med. 2014, 71, 196-207
26. Klomsiri, C.; Karplus, P. A.; Poole, L. B. Antioxid. Redox Signaling 2011, 14, 1065-1077
27. Mieyal, J. J.; Chock, P. B. Antioxid. Redox Signaling 2012, 16, 471-475
28. Ursini, F.; Maiorino, M.; Forman, H. J. Redox Biol. 2016, 8, 205-215
29. Brigelius-Flohé, R.; Flohé, L. Antioxid. Redox Signaling 2011, 15, 2335-2381
30. Holmstrom, K. M.; Finkel, T. Nat. Rev. Mol. Cell Biol. 2014, 15, 411-421
31. Kim, E.; Liu, Y.; Leverage, W. T.; Yin, J.-J.; White, I. M.; Bentley, W. E.; Payne, G. F. Biomacromolecules 2014, 15, 1653-1662
32. Kim, E.; Panzella, L.; Micillo, R.; Bentley, W. E.; Napolitano, A.; Payne, G. F. Sci. Rep. 2015, 5, 18447
33. Wang, J. Electroanalysis 2001, 13, 983-988
34. George, P.; Irvine, D. H. Biochem. J. 1954, 58, 188-195
35. Muller, J. G.; Duarte, V.; Hickerson, R. P.; Burrows, C. J. Nucleic Acids Res. 1998, 26, 2247-2249
36. Lüthje, S.; Bottger, M. Biochim. Biophys. Acta, Bioenerg. 1989, 977, 335-340
37. Bhattarai, N.; Stanbury, D. M. Inorg. Chem. 2012, 51, 13303-13311
38. Drury, W. D.; Dekorte, J. M. Inorg. Chem. 1983, 22, 121-125
39. Kottapalli, K. K.; Adari, K. K.; Vani, P.; Govindan, S. K. Transition Met. Chem. 2005, 30, 773-777
40. van Os, J.; Kapur, S. Lancet 2009, 374, 635-645
41. Gilca, M.; Piriu, G.; Gaman, L.; Delia, C.; Iosif, L.; Atanasiu, V.; Stoian, I. Psychopharmacology 2014, 231, 4703-4710
42. Kulak, A.; Steullet, P.; Cabungcal, J.-H.; Werge, T.; Ingason, A.; Cuenod, M.; Do, K. Q. Antioxid. Redox Signaling 2013, 18, 1428-1443
43. Yao, J. K.; Keshavan, M. S. Antioxid. Redox Signaling 2011, 15, 2011-2035
44. Metters, J. P.; Kadara, R. O; Banks, C. E. Analyst 2011, 136, 1067-1076
45. Bhattarai, N.; Stanbury, D. M. J. Phys. Chem. B 2014, 118, 1097-1101
46. Mailloux, R. J.; McBride, S. L.; Harper, M.-E. Trends Biochem. Sci. 2013, 38, 592-602
47. Loi, V. V.; Rossius, M.; Antelmann, H. Front. Microbiol. 2015, 6,
48. Apak, R.; Özyürek, M.; Güçlü, K.; Çapanoğlu, E. J. Agric. Food Chem. 2016, 64, 997-1027
49. Cao, G.; Prior, R. L. Clin. Chem. 1998, 44, 1309-1315
50. Rice-Evans, C.; Miller, N. J. In Oxygen Radicals in Biological Systems, Part D; Methods in Enzymology, Vol. 234; Academic Press: San Diego, CA, 1994; pp 279-293.
51. Ran, X.; Sun, H.; Pu, F.; Ren, J.; Qu, X. Chem. Commun. 2013, 49, 1079-1081
52. Ge, J.; Huang, Z.-M.; Xi, Q.; Yu, R.-Q.; Jiang, J.-H.; Chu, X. Chem. Commun. 2014, 50, 11879-11882
53. Niu, L.-Y.; Chen, Y.-Z.; Zheng, H.-R.; Wu, L.-Z.; Tung, C.-H.; Yang, Q.-Z. Chem. Soc. Rev. 2015, 44, 6143-6160
54. Jung, H. S.; Chen, X.; Kim, J. S.; Yoon, J. Chem. Soc. Rev. 2013, 42, 6019-6031
55. Liu, Z.; Liu, Y.; Kim, E.; Bentley, W. E.; Payne, G. F. Anal. Chem. 2016, 88, 7213-7221
56. Dickinson, B. C.; Chang, C. J. Nat. Chem. Biol. 2011, 7, 504-511
57. Wasil, M.; Halliwell, B.; Hutchison, D. C. S.; Baum, H. Biochem. J. 1987, 243, 219
58. Carballal, S.; Radi, R.; Kirk, M. C.; Barnes, S.; Freeman, B. A.; Alvarez, B. Biochemistry 2003, 42, 9906-9914
59. Albayrak, Y.; Ünsal, C.; Beyazyüz, M.; Ünal, A.; Kuloğlu, M. Prog. Neuro-Psychopharmacol. Biol. Psychiatry 2013, 45, 144-149
60. Zhang, X. Y.; Chen, D. C.; Xiu, M. H.; Tang, W.; Zhang, F.; Liu, L.; Chen, Y.; Liu, J.; Yao, J. K.; Kosten, T. A.; Kosten, T. R. Schizophr. Res. 2012, 139, 66-72
61. Flatow, J.; Buckley, P.; Miller, B. J. Biol. Psychiatry 2013, 74, 400-409
62. Schwarz, E.; Izmailov, R.; Spain, M.; Barnes, A.; Mapes, J. P.; Guest, P. C.; Rahmoune, H.; Pietsch, S.; Leweke, F. M.; Rothermundt, M.; Steiner, J.; Koethe, D.; Kranaster, L.; Ohrmann, P.; Suslow, T.; Levin, Y.; Bogerts, B.; van Beveren, N.; McAllister, G.; Weber, N.; Niebuhr, D.; Cowan, D.; Yolken, R. H.; Bahn, S. Biomark. Insights 2010, 5, 39-47
63. Yu, B. P. Physiol. Rev. 1994, 74, 139-162

64. Costa, C. M. d.; Santos, R. C. C. d.; Lima, E. S. J. Bras. Patol. Med. Lab. 2006, 42, 345-350
65. Sedlak, J.; Lindsay, R. H. Anal. Biochem. 1968, 25, 192-205
66. Gordonov, T.; Kim, E.; Cheng, Y.; BenYoav, H.; Ghodssi, R.; Rubloff, G.; Yin, J.-J.; Payne, G. F.; Bentley, W. E. Nat. Nanotechnol. 2014, 9, 605-610
67. Laksanasopin, T.; Guo, T. W.; Nayak, S.; Sridhara, A. A.; Xie, S.; Olowookere, O. O.; Cadinu, P.; Meng, F.; Chee, N. H.; Kim, J.; Chin, C. D.; Munyazesa, E.; Mugwaneza, P.; Rai, A. J.; Mugisha, V.; Castro, A. R.; Steinmiller, D.; Linder, V.; Justman, J. E.; Nsanzimana, S.; Sia, S. K. Sci. Transl. Med. 2015, 7, 273re1
68. Bewick, V.; Cheek, L.; Ball, J. Critical Care 2004, 8, 46
69. Hekimi, S.; Lapointe, J.; Wen, Y. Trends Cell Biol. 2011, 21, 569-576
70. Yao, J. K.; Leonard, S.; Reddy, R. Dis. Markers 2006, 22, 83-93
71. Yao, J. K.; Reddy, R.; van Kammen, D. P. Psychiatry Res. 2000, 97, 137-151
72. Overall, J. E.; Gorham, D. R. Psychol. Rep. 1962, 10, 799-812
73. Pelizzetti, E.; Mentasti, E.; Baiocchi, C. J. Phys. Chem. 1976, 80, 2979-2982
74. Apak, R.; Güçlü, K.; Özyürek, M.; Karademir, S. E. n.; Altun, M. Free Radical Res. 2005, 39, 949-961
75. Apak, R.; Güçlü, K.; Özyürek, M.; Çelik, S. E. Microchim. Acta 2008, 160, 413-419 DOI: 10.1007/s00604-007-0777-0

What is claimed:

1. A method for determining a redox-based condition associated with oxidative stress, using a measuring device, the method comprising:
    contacting a sample from a patient at a point-of-care with one or more redox-mediators defining a redox potential;
    providing an electrical input to the sample, the electrical input being a sequence having:
        a first input pulse defined by a first oxidative voltage greater than the redox potential and imposed for a first duration; and
        at least a second input pulse defined by a second oxidative voltage equal to the first oxidative voltage and imposed for a second duration different than the first duration, the first input pulse and the at least second input pulse being separated by an off voltage, the off voltage being imposed for a duration greater than the first duration;
    measuring by electrodes a dynamic pattern of current and charge over a period of time of the sample based on the one or more redox-mediators and the electrical input;
    measuring by an optical sensor an optical output over the period of time of the sample based on the one or more redox-mediators and the electrical input; and
    using the dynamic pattern of current and charge and the optical output over the period of time to derive a plurality of electrochemical or spectroelectrochemical pattern signal signatures for determining the redox-based condition, thereby assaying for a presence of the redox-based condition associated with oxidative stress within the patient at the point-of-care.

2. The method of claim 1, further comprising:
    comparing the plurality of electrochemical or spectroelectrochemical pattern signal signatures in the sample to an electrochemical or spectroelectrochemical pattern signal signature of a control sample, by an identification module programmed to identify executable code of the plurality of electrochemical or the spectroelectrochemical pattern signal signatures that is to be analyzed, wherein the electrochemical or spectroelectrochemical pattern signal signature of the control sample is stored in a database; and
    analyzing, by an analyzer, a result of the comparison to identify a presence of a marker of interest within the sample.

3. The method of claim 2, wherein the determining is performed by the analyzer, and wherein the method further includes:
    training the analyzer to identify and correlate the spectroelectrochemical pattern signal signature that discriminates the sample and control data set; and
    autonomously adjusting, by the analyzer, the electrical input to the sample to determine a second electrical input that generates signatures with greater discriminating capabilities than discriminating capabilities of the electrical input to the sample.

4. The method of claim 1, wherein the sample is a biological sample derived from the patient.

5. The method of claim 4, wherein the biological sample is a blood, sweat, urine, saliva, or serum sample.

6. The method of claim 5, wherein the sample is the serum sample.

7. The method of claim 4, further comprising:
    adjusting a treatment based on the determined presence of the redox-based condition.

8. The method of claim 1, wherein the redox-based condition is associated with an oxidative stress disorder, redox dysregulation, or inflammation.

9. The method of claim 8, wherein the redox-based condition is schizophrenia.

10. The method of claim 1, wherein the one or more redox-mediators are selected from the group consisting of iridium, ferrocene, ferricyanide, ruthenium, osmium, rhodium, copper, cobalt, nickel, chromium, platinum and palladium, redox-active organic molecules, and radical precursors.

11. The method of claim 10, wherein the one or more redox-mediators include an iridium salt.

12. The method of claim 11, wherein the one or more redox-mediators includes $K_2IrCl_6$ ($Ir^{OX}$).

13. A method for detecting the presence of an oxidative stress disorder from a signal signature comprising:
    contacting a sample with one or more redox-mediators defining a redox potential, wherein the sample is a biological sample derived from a subject at a point-of-care;
    providing an electrical input to the sample, the electrical input being a sequence having oxidative and reductive pulses including:
        a first input pulse defined by a first oxidative voltage greater than the redox potential and imposed for a first duration;
        a second input pulse defined by a second oxidative voltage equal to the first oxidative voltage and imposed for a second duration different than the first duration, the first input pulse and the second input pulse being separated by a first off voltage, the first off voltage being imposed for a duration greater than the first duration; and
        a third input pulse with a second off voltage between the second input pulse and the third input pulse, the third input pulse defined by a third oxidative voltage equal to the first oxidative voltage and a fourth oxidative voltage less than the third oxidative voltage, the third and fourth oxidative voltages bracketing the redox potential of the one or more redox mediators;

measuring by electrodes a dynamic pattern of current and charge continuously over a period of time of the sample based on the one or more redox-mediators and the electrical input;

measuring by an optical sensor an optical output continuously over the period of time of the sample based on the one or more redox-mediators and the electrical input; and using the dynamic pattern of current and charge and the optical output over the continuous period of time to derive a plurality of electrochemical or spectroelectrochemical pattern signal signatures for determining the presence of the oxidative stress disorder, thereby assaying for the presence of the oxidative stress disorder within the subject at the point-of-care.

14. The method of claim 13, wherein the one or more redox-mediators includes $K_2IrCl_6$ ($Ir^{OX}$).

15. The method of claim 13, wherein the measuring by the electrodes and the optical sensor includes simultaneous measuring by a perforated electrode; and using a dynamic pattern of current and charge and the optical output over the continuous period of time to derive signal metrics including: a charge transfer; the charge, the optical output, a cross-modal response between the charge and the optical output, and a first order rate for decay in the optical output.

16. A method of redox probing to access global chemical information on oxidative stress from a serum sample from a patient at a point-of-care, the method comprising:

diluting the serum sample at the point-of-care with an iridium-based redox-mediator having a redox potential to define an assay with sensitivity to glutathione (GSH);

providing a three pulse-redox-relaxation sequence electrical input to the diluted serum sample by dropping the diluted serum sample onto a screen-printed electrode system at the point-of-care;

capturing at the point-of-care an optical signal and an electrical signal as a redox-state-dependent output response to the three pulse-redox-relaxation sequence electrical input in contact with the diluted serum sample, the three pulse-redox-relaxation sequence electrical input including:
  a first input pulse defined by a first on-voltage that is greater than the redox potential and imposed for a duration of one minute;
  a second input pulse defined by a second on-voltage that is greater than the redox potential and imposed for a duration of three minutes, the first and second input pulses separated by an off-voltage applied for a duration that allows the optical signal to decay; and
  a third input pulse defined by a third on-voltage that is greater than the redox potential and imposed for a duration of three minutes, and a fourth on-voltage that is less than the redox potential and imposed for a duration of three minutes;

accessing the global chemical information on oxidative stress from the redox-state-dependent output response, the global chemical information being defined by a plurality of quantitative metrics relevant to oxidative stress, including:
  determining over the duration of each of the first input pulse, second input pulse and third input pulse each of (i) a charge transferred; (ii) an optical absorbance; and (iii) a cross-modal response defined as a slope between the optical signal and the electrical signal;
  determining a first-order rate constant for the decay of the optical signal over the duration of the off-voltage; and
  determining for the third input pulse a ratio of the charge transfer at the third on-voltage over the charge transfer at the fourth on-voltage.

* * * * *